(12) United States Patent
Hart et al.

(10) Patent No.: US 7,790,420 B2
(45) Date of Patent: Sep. 7, 2010

(54) METHOD FOR DETERMINING PROTEIN SOLUBILITY

(75) Inventors: Darren Hart, Cedex (FR); Franck Tarendeau, Cedex (FR)

(73) Assignee: European Molecular Biology Laboratory, Heidelburg (DE)

(*) Notice: Subject to any disclaimer, the term of this patent is extended or adjusted under 35 U.S.C. 154(b) by 0 days.

(21) Appl. No.: 11/700,820

(22) Filed: Feb. 1, 2007

(65) Prior Publication Data

US 2007/0224618 A1 Sep. 27, 2007

Related U.S. Application Data

(63) Continuation-in-part of application No. PCT/GB2005/003417, filed on Sep. 5, 2005.

(30) Foreign Application Priority Data

Sep. 3, 2004 (GB) .................. 0419628.3

(51) Int. Cl.
C12N 15/64 (2006.01)
C12N 15/74 (2006.01)
C12P 21/06 (2006.01)
C40B 50/06 (2006.01)

(52) U.S. Cl. ............ 435/91.42; 506/26; 435/91.4; 435/471; 435/69.1

(58) Field of Classification Search ............ 435/91.42, 435/91.4, 471, 69.1; 506/26
See application file for complete search history.

(56) References Cited

U.S. PATENT DOCUMENTS 7,332,308 B1 * 2/2008 Benkovic et al. ......... 435/91.42

2002/0132349 A1 * 9/2002 Goryshin et al. ............ 435/473
2004/0132971 A1 * 7/2004 Haaning et al. ............. 530/350

FOREIGN PATENT DOCUMENTS

WO WO 2006024875 * 3/2006

OTHER PUBLICATIONS

Ostermeier et al., 1999, Combinatorial protein engineering by incremental truncation, PNAS, 96: 3562-3567.*
Ostermeier et al., 2003, The creation of ITCHY hybrid protein libraries, Methods in Molecular Biology, 231: 129-141.*
Lutz et al., 2001, Creating multiple-crossover DNA libraries independent of sequence identity, PNAS, 98(20): 11248-11253.*
Ostermeier et al., 1999, A combinatorial approach to hybrid enzymes independent of DNA homology, Nature Biotechnology, 17: 1205-1209.*
Lutz et al., 2001, Rapid generation of incremental truncation libraries for protein engineering using a-phosphothioate nucleotides, Nucleic Acids Research, 29(4): 7 pages.*
D Beckett et al., "A minimal peptide substrate in biotin holoenzyme synthetase-catalyzed biotinylation", *Protein Science*, vol. 8, pp. 921-929, 1999.

* cited by examiner

*Primary Examiner*—Amber D. Steele
(74) *Attorney, Agent, or Firm*—Wenderoth, Lind & Ponack, L.L.P.

(57) ABSTRACT

The present invention relates to methods of screening for expression of a soluble candidate protein within an expression library of candidate proteins. The method involves fusing each candidate protein in the library to a peptide substrate and identifying cells that express soluble candidate protein by detecting enzymatic modification of the peptide substrate.

15 Claims, 27 Drawing Sheets

SEQUENCE LISTING

<160> NUMBER OF SEQ ID NOS: 21

<210> SEQ ID NO 1
<211> LENGTH: 15
<212> TYPE: PRT
<213> ORGANISM: Artificial

```
<220> FEATURE:
<223> OTHER INFORMATION: Synthetic construct

<400> SEQUENCE: 1

Gly Leu Asn Asp Ile Phe Glu Ala Gln Lys Ile Glu Trp His Glu
1               5                   10                  15

<210> SEQ ID NO 2
<211> LENGTH: 10
<212> TYPE: PRT
<213> ORGANISM: Artificial
<220> FEATURE:
<223> OTHER INFORMATION: Synthetic construct

<400> SEQUENCE: 2

Arg Arg Arg Asp Asp Asp Ser Asp Asp Asp
1               5                   10

<210> SEQ ID NO 3
<211> LENGTH: 66
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (40)..(66)
<223> OTHER INFORMATION: n is A, T, C or G and indicates a complementary
      base to the candidate gene sequence omitting the ATG start codon

<400> SEQUENCE: 3
gatcctagca tatgaaatgc atggatccgc ggccgctgan nnnnnnnnnn nnnnnnnnn      60 nnnnnn                                                                66

<210> SEQ ID NO 4
<211> LENGTH: 24
<212> TYPE: DNA
<213> ORGANISM: Artificial
<220> FEATURE:
<223> OTHER INFORMATION: Synthetic construct

<400> SEQUENCE: 4
gatcctagca tatgaaatgc atgg                                            24

<210> SEQ ID NO 5
<211> LENGTH: 43
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (17)..(43)
<223> OTHER INFORMATION: n is A, T, C or G and indicates a complementary
      base to the candidate gene sequence omitting the ATG start codon

<400> SEQUENCE: 5
gatcctaggg ccggccnnnn nnnnnnnnnn nnnnnnnnnn nnn                       43

<210> SEQ ID NO 6
<211> LENGTH: 21
<212> TYPE: DNA
<213> ORGANISM: Artificial
<220> FEATURE:
<223> OTHER INFORMATION: Synthetic construct
<220> FEATURE:
<221> NAME/KEY: misc_feature
<222> LOCATION: (17)..(21)
```

-continued

<223> OTHER INFORMATION: n is A, T, C or G and indicates a complementary
     base to the candidate gene sequence omitting the ATG start codon

<400> SEQUENCE: 6
gatcctaggg ccggccnnnn n                                              21

<210> SEQ ID NO 7
<211> LENGTH: 67
<212> TYPE: DNA
<213> ORGANISM: Artificial
<220> FEATURE:
<223> OTHER INFORMATION: Synthetic construct

<400> SEQUENCE: 7
agcttgcttg gtggcggtct gaacgacatc ttcgaggctc agaaaatcga atggcacgaa    60
taatgag                                                              67

<210> SEQ ID NO 8
<211> LENGTH: 67
<212> TYPE: DNA
<213> ORGANISM: Artificial
<220> FEATURE:
<223> OTHER INFORMATION: Synthetic construct

<400> SEQUENCE: 8
agctctcatt attcgtgcca ttcgattttc tgagcctcga agatgtcgtt cagaccgcca    60
ccaagca                                                              67

<210> SEQ ID NO 9
<211> LENGTH: 48
<212> TYPE: DNA
<213> ORGANISM: Artificial
<220> FEATURE:
<223> OTHER INFORMATION: Synthetic construct

<400> SEQUENCE: 9
ggatccgcgg ccgctgagca gatggcccat accttcaaat attagagc                 48

<210> SEQ ID NO 10
<211> LENGTH: 43
<212> TYPE: DNA
<213> ORGANISM: Artificial
<220> FEATURE:
<223> OTHER INFORMATION: Synthetic construct

<400> SEQUENCE: 10
gggatccggc cggccccttc tgacgtttcc tctgcacttc ttc                      43

<210> SEQ ID NO 11
<211> LENGTH: 18
<212> TYPE: DNA
<213> ORGANISM: Artificial
<220> FEATURE:
<223> OTHER INFORMATION: Synthetic construct

<400> SEQUENCE: 11
acaggacagc tggatgtg                                                  18

<210> SEQ ID NO 12
<211> LENGTH: 18
<212> TYPE: DNA
<213> ORGANISM: Artificial
<220> FEATURE:
<223> OTHER INFORMATION: Synthetic construct

```
<400> SEQUENCE: 12
acttgaaaat tgtaagaa                                                 18

<210> SEQ ID NO 13
<211> LENGTH: 18
<212> TYPE: DNA
<213> ORGANISM: Artificial
<220> FEATURE:
<223> OTHER INFORMATION: Synthetic construct

<400> SEQUENCE: 13
atgcatccaa cttgaaaa                                                 18

<210> SEQ ID NO 14
<211> LENGTH: 18
<212> TYPE: DNA
<213> ORGANISM: Artificial
<220> FEATURE:
<223> OTHER INFORMATION: Synthetic construct

<400> SEQUENCE: 14
cccccaatgc atccaact                                                 18

<210> SEQ ID NO 15
<211> LENGTH: 18
<212> TYPE: DNA
<213> ORGANISM: Artificial
<220> FEATURE:
<223> OTHER INFORMATION: Synthetic construct

<400> SEQUENCE: 15
atgacagtaa agccccca                                                 18

<210> SEQ ID NO 16
<211> LENGTH: 18
<212> TYPE: DNA
<213> ORGANISM: Artificial
<220> FEATURE:
<223> OTHER INFORMATION: Synthetic construct

<400> SEQUENCE: 16
acgccatcta tgacagta                                                 18

<210> SEQ ID NO 17
<211> LENGTH: 18
<212> TYPE: DNA
<213> ORGANISM: Artificial
<220> FEATURE:
<223> OTHER INFORMATION: Synthetic construct

<400> SEQUENCE: 17
cagacgccat ctatgaca                                                 18

<210> SEQ ID NO 18
<211> LENGTH: 18
<212> TYPE: DNA
<213> ORGANISM: Artificial
<220> FEATURE:
<223> OTHER INFORMATION: Synthetic construct

<400> SEQUENCE: 18
tatcagacgc catctatg                                                 18

<210> SEQ ID NO 19
<211> LENGTH: 18
```

```
<212> TYPE: DNA
<213> ORGANISM: Artificial
<220> FEATURE:
<223> OTHER INFORMATION: Synthetic construct

<400> SEQUENCE: 19
ccgtggtatc agacgcca                                                          18

<210> SEQ ID NO 20
<211> LENGTH: 97
<212> TYPE: DNA
<213> ORGANISM: Artificial
<220> FEATURE:
<223> OTHER INFORMATION: Synthetic construct

<400> SEQUENCE: 20
acccgtggta tcagacgcca tctatgacag taaagccccc aatgcatcca acttgaaaat            60
tgtaagaatg gacaggacag ctggatgtgt gactgga                                     97

<210> SEQ ID NO 21
<211> LENGTH: 32
<212> TYPE: PRT
<213> ORGANISM: Artificial
<220> FEATURE:
<223> OTHER INFORMATION: Synthetic construct

<400> SEQUENCE: 21

Pro Val Val Ser Asp Ala Ile Tyr Asp Ser Lys Ala Pro Asn Ala Ser
 1               5                  10                  15

Asn Leu Lys Ile Val Arg Met Asp Arg Thr Ala Gly Cys Val Thr Gly
             20                  25                  30
```

METHOD FOR DETERMINING PROTEIN SOLUBILITY

This application is a continuation-in-part of International Application No. PCT/GB2005/003417 filed Sep. 5, 2005.

The present invention relates to methods of screening for expression of a soluble candidate protein within an expression library of candidate proteins. The method involves fusing each candidate protein in the library to a peptide substrate and identifying cells that express soluble candidate protein by detecting enzymatic modification of the peptide substrate.

All publications, patents and patent applications cited herein are incorporated in full by reference.

BACKGROUND TO THE INVENTION

Structural genomics has gained increasing interest in recent years. The elucidation of protein structures is important to enhance the understanding of protein function and thereby facilitate pharmaceutical drug development.

Protein expression and purification are key processes in such studies, and are often limited by the ability to produce properly folded recombinant protein. The preparation of proteins for structural and functional analysis using the *Escherichia coli* (*E. coli*) expression system is often hampered by the formation of insoluble intracellular protein aggregates (inclusion bodies), degradation by proteases or lack of expression.

*E. coli* is a common expression host that often makes misfolded protein when obliged to overproduce non-native gene products. This severely limits the usefulness of the protein in areas such as structural analysis by crystallography and NMR and limits the overall success rate of current structural genomics projects. Conventional approaches to problem of insoluble expressed proteins include low-temperature expression, the use of promoters with different strengths, a variety of solubility-enhancing fusion tags (Kapust R B & Waugh D S. '*Escherichia coli* maltose-binding protein is uncommonly effective at promoting the solubility of polypeptides to which it is fused'. *Protein Sci.* 1999 August; 8(8) 1668-74) and modified growth media (Makrides S C 'Strategies for achieving high-level expression of genes in *Escherichia coli*'. *Microbiol Rev.* 1996 September; 60 (3): 512-38. Review).

Another approach for overcoming this difficulty is through structure prediction from the amino acid sequence of the protein of interest. Information such as homology alignments and secondary structure prediction is used to predict the position of stable, soluble domains. A truncation or mutation of the target protein is first constructed and then expressed and tested for solubility. Despite continuous progress, the purely 'rational' design of proteins with desired properties, such as stability or soluble expression, is, at least to date, not generally feasible. Even in the presence of extensive structural and mechanistic information, it is difficult to predict the necessary sequence truncation required. There is still little information as to how amino acid sequence affects every aspect of protein structure, from its ability to be expressed in a heterologous host to its ability to fold in non-native environments. Experiments have demonstrated that changes in protein properties are brought about by the cumulative effects of many small adjustments, many of which are distributed or propagated over significant distances within the protein molecule and bioinformatic programs are currently unable to predict accurately which truncations or mutations will increase protein solubility.

In normal structural projects, several tens of clones may be constructed and tested for soluble protein expression. With such projects, the possible diversity is greatly undersampled and often solutions are not found. Additionally, with many proteins predicted from genome sequences there are no known homologues and this limits the effectiveness of bioinformatics approaches. High throughput screening strategies can prove effective for discovering soluble constructs when standard approaches fail. These require the accurate analysis of large numbers of expression clones to identify suitable constructs for structure determination. If the whole protein does not express or crystallise, the next step is to generate truncations or random mutations and retest.

Although (i) current methodologies permit the creation of very large expression libraries; and (ii) the chances that a library contains a soluble protein increases with the size of the library, the practical limits imposed by current approaches for screening expression libraries restricts this practice. The ultimate aim of experimenters who wish to express a soluble or crystallisable form of a protein of interest is to synthesise all possible variants of a target protein and screen them for soluble expression. Clones expressing soluble protein can be used directly, or can be used to seed the next round of library construction and selection. Such experiments would yield a massive number of clones, which would then have to be screened for the expression of soluble target protein.

Several systems have been described that have the aim of identifying soluble variants of a candidate protein of interest (generated by random mutagenesis or truncation). In fusion reporter methods, a candidate protein and a reporter protein with an easily detectable feature or biological activity are expressed as a genetic fusion. Information about the folding state of the protein can be derived from a screenable or selectable activity by the fused reported domain.

Fusion reporter methods usually involve fusion of a C-terminal partner "solubility reporter" (e.g. green fluorescent protein (GFP), Chloramphenicol acetyl transferase (CAT) or beta galactosidase. In the GFP fusion reporter method, the fluorescent yield of GFP provides information about the folding state of its fusion partner. Cells expressing GFP fused to a poorly folded insoluble protein fluoresce less brightly than those expressing GFP fused to a well-folded soluble protein. GFP monitors the folding yield of the test protein, which is subsequently expressed without the GFP tag (Waldo G S 'Genetic screens and directed evolution for protein solubility'. *Curr Opin Chem Biol.* 2003 February; 7(1):33-8. Review).

The inventor has previously developed a fusion reporter system based on the use of biotin carboxyl carrier protein (BCCP) as a protein-folding marker. In this system, the biotinylation domain of BCCP from *E. coli* is fused to a test protein. The correctly folded secondary and tertiary structure of this domain is recognised by endogenous host cell biotin protein ligase which biotinylates the domain. Host cells expressing correctly folded test protein and BCCP domain will test positive for the presence of the biotin group (WO03/064656 'Protein tag comprising a biotinylation domain and method for increasing solubility and determining folding state').

However, there are problems associated with these systems, which limit their applicability.

The use of autonomously folding reporter proteins (e.g. GFP, CAT, beta-gal or BCCP domain) can generate problematic false positive rates due to their large and soluble nature. This can generate overwhelming false positive rates because the reporter can tolerate fusion of otherwise insoluble protein X fragments or full-length proteins without itself becoming insoluble. This may not be a problem when the tag can be left in place e.g. when immobilising proteins via the tag or performing biochemical analyses on the purified protein, but many applications e.g. protein crystallography, require removal of the tag by protease cleavage or genetic deletion; much time and expense is lost by processing clones that subsequently aggregate or degrade upon tag removal and are therefore unusable. It is also possible for the fusion protein to be degraded by proteolysis during expression in vivo, which leaves a soluble fluorescent reporter molecule that generates false positive results.

These effects are very commonly observed with fusion proteins such as those containing maltose binding protein, glutathione-S-transferase, GFP, thioredoxin and is presumably a general effect. Thus, the presence of a highly soluble fusion partner acting as a solubility reporter strongly perturbs the solubility of what it is fused to.

Furthermore, most of the fusion proteins disclosed in the prior are large proteins. For example, fusion of GFP increases the size of the protein by approximately 37 kDa. Expression of large fusion proteins in E. coli. is problematic, with a practical limitation of about 100 kDa.

Simulation studies, when combined with experiments and sequence/structure database analyses, can help delineate major evolutionary factors responsible for shaping proteins. However, the potential of such studies has not as yet been fully explored.

Accordingly, there thus exists a great need in the art for the development of a method for rapid, high throughput and reliable screening of the expressed proteins as early as possible in the overall process from cloning to structure determination, allowing the selection of soluble expressed proteins. Suitable methods should allow the high throughput screening of a large number of molecules containing different variant sequences, with the selection process allowing the easy identification of molecules with improved solubility. The amenability of such a method to the high throughput analysis of an expression library of variants of individual proteins, especially when used in combination with a mutation or truncation procedure strategy, to enable the identification and isolation of soluble variants of insoluble proteins would make the optimisation of high level expression of a problematic protein more affordable and less laborious. Additionally, the method should seek to i) minimise the pertubatory effects of any fusion partner and ii) should minimise the downstream steps required for structural analysis such as removal of the fused tag; proteins are routinely crystallised with small peptide tags but rarely as bidomain fusions.

SUMMARY OF THE INVENTION

This invention embraces mechanisms by which soluble variants of an insoluble protein may be selected. In these mechanisms the coding region of an insoluble protein can be manipulated, translated and expressed to determine whether a particular manipulation produces a soluble variant. Accordingly, the factors that affect the solubilization of the insoluble protein can be identified by sequencing of its encoding nucleic acid molecule. The mechanisms thus also give important insights into the protein features that impact on solubility.

According to one aspect of the invention, there is provided a method of screening for a soluble candidate protein within a plurality of variant candidate proteins wherein each candidate protein is fused to a peptide substrate such that a soluble candidate protein is identified by the detection of an enzymatic modification of the peptide substrate.

This novel method does not rely on the peptide substrate itself exhibiting some kind of testable activity, such as inherent fluorescence in the case of GFP or enzymatic turnover in the case of chloramphenicol acetyl transferase. The underlying principle behind the use of such a peptide as a solubility reporter is that only soluble molecules are efficient substrates for enzymes. Therefore, only if the peptide is fused to a soluble candidate protein, can it act as a direct substrate for an enzyme with no need for folding of the peptide itself. If, however, it is fused to an insoluble protein, its interaction with the peptide-modifying enzyme active site is severely restricted for steric and diffusional reasons and negligible enzymatic modification will occur resulting in a negative, unmodified phenotype. Additionally, if peptides are expressed in isolation in E. coli, (as would happen if fused out of frame to a gene or gene fragment) they are generally unstable, proteolysed and therefore removed from the cell, again resulting in a default negative phenotype. The method is amenable to the high throughput analysis of an expression library, for example, when used in combination with a protein truncation strategy. Because a large number of variants are made and tested in a single procedure, this greatly increases the chances of successfully identifying a soluble, and ideally highly expressed, candidate protein.

The peptide substrate is small and inert and thus does not significantly alter the physical characteristics of the candidate protein to which it is fused. In this case the term 'not significant', or variants thereof, in relation to an alteration of a physical characteristic means a variance of between +/−50% or less of the physical characteristic, for example +/−45% or less, +/−40% or less, +/−35% or less, +/−30% or less, +/−25% or less, +/−20% or less, +/−15% or less, +/−13% or less, +/−10% or less, or smaller. Preferably, the peptide substrate does not alter the physical characteristics of the candidate protein to which it is fused. Such physical characteristics include solubility, size, charge, folding and assembly mechanism of the candidate protein. A particular advantage is that the solubility of the candidate protein is neither perturbed nor enhanced. This limits the occurrence of false positive results, that are common in the methodologies of the prior art and are associated with the use of large, folded, soluble reporter molecules which will tolerate fusion of otherwise insoluble protein fragments.

A further advantage of the invention is that the methodology allows a quantitative analysis of the yield and solubility of candidate proteins to be made as well as a qualitative analysis. This allows a user to select clones encoding particularly soluble candidate proteins for analysis and/or further steps of manipulation and screening.

The term 'candidate protein' as used herein may be any protein or peptide, synthetic or naturally-occurring, including protein fragments, polypeptides, multimeric proteins, recombinant proteins, fusion and hybrid proteins, antibodies, and so on.

According to the invention a 'peptide substrate' includes any short region of peptide comprising amino acids joined to each other by peptide bonds or modified peptide bonds, i.e. peptide isosteres. This term refers both to short peptide chains of between 5 and 20 amino acids, as well as longer oligopeptide chains, of between 20 and 50 amino acids. Such peptides can be fused to a candidate protein and must be capable of functioning as a substrate for an enzyme, such that the peptide substrate becomes modified by enzymatic action when soluble.

As the skilled person will appreciate, enzymatic modification of the peptide substrate is not binary. That is, the state of the peptide substrate is not either soluble or insoluble, instead there are degrees of solubility which affect the level at which the peptide substrate can be enzymatically modified. The difference between efficient and inefficient modification can, therefore, be assessed and a subset of potentially useful constructs arrived at.

Preferably, the peptide substrate is small in relation to the candidate protein to which it is fused. For example, in the case of large candidate proteins, is not so important that the size of the peptide substrate be diminishingly small, and slightly longer peptide substrates may be tolerated without perturbing the structure of the candidate protein and thus leading to false positive results. In contrast, in the case of small candidate proteins, the peptide substrate should ideally be as small as possible. Preferably, the length of the peptide substrate does not exceed 20% of the length of the candidate protein; more preferably, it does not exceed 15% of the length of the candidate protein; even more preferably, it does not exceed 10% of the length of the candidate protein; and even more preferably, it is less than 5% of the length of the candidate protein.

Preferably the peptide substrate is short, being 50 amino acids in length or smaller, for example, 45 or less, 40 or less, 35 or less, 30 or less, 25 or less, 20 or less, 15 or less, 13 or less, 10 or less, or smaller.

Preferably, the peptide substrate is linear and possesses no tertiary structure. By this is meant that the peptide does not fold into a structured, three-dimensional arrangement of secondary structure motifs.

Preferred peptide substrates include peptides that act as substrates for biotin protein ligase. One example of such a peptide substrate is the 15 amino acid peptide characterised by Schatz (1993) and Beckett et al. (1999) [Schatz P J (1993) Use of peptide libraries to map substrate specificity of a peptide-modifying enzyme: a 13 residue consensus peptide specifies biotinylation in *Escherichia coli* Biotechnology, 11 138-1143; Becket et al. (1999) A minimal peptide substrate in biotin holoenzyme synthetase-catalysed biotinylation Protein Science 8 921-929]. The sequence of this peptide is GLNDIFEAQKIEWHE (SEQ ID NO: 1) and several close variants also exist. When fused to a soluble protein, the peptide acts as a substrate for biotin protein ligase, an enzyme that transfers a biotin molecule from biotin-AMP to the lysine residue of this sequence that is underlined. When unfused, or fused to an insoluble partner, it is a very inefficient substrate. The use of peptide substrates that are substrates for biotin protein ligase allows proteins to be screened for solubility by detection with streptavidin conjugates. For example, a Western-type or dot-blot might be used in which streptavidin-peroxidase conjugates can be detected with chemiluminescence or directly using a fluorescently labelled streptavidin and a fluorimager instrument e.g. an Amersham Typhoon. Other compounds that are capable of binding to biotin include neutravidin, avidin and monomeric avidin.

Preferred peptide substrates also include peptides that act as substrates for a coexpressed kinase such as, for example, casein kinase II, a ubiquitous serine/threonine protein kinase found in eukaryotic cells. When fused to a soluble protein, the peptide (e.g. RRRDDDSDDD (SEQ ID NO: 2)) acts as a substrate for the kinase and becomes phosphorylated at a specific residue (S).

As previously described, when unfused, or fused to an insoluble partner, efficient phosphorylation of the peptide does not occur. Phosphorylated peptide substrates are detected using a specific antiphosphoantibody. Binding of the antiphosphoantibody to the phosphopeptide may be detected directly e.g. using a fluorescently labelled antiphosphoantibody conjugate.

As the skilled reader will appreciate, there are a number of ways in which the peptide substrate may be fused to the candidate protein. For example, the peptide substrate may be fused to the candidate protein by non-covalent bonds. The peptide substrate may be fused to the candidate protein post-translationally e.g. by intein biology. Preferably, the peptide substrate may be fused to the candidate protein by covalent bonds, for example, through a peptide bond, through chemical linkage and so on. Preferably, the peptide substrate is expressed as a genetic fusion, forming a recombinant fusion protein with the candidate protein. In cases of such genetic fusions, the attachment of the peptide substrate and the candidate protein components may preferably be achieved using a recombinant DNA construct that encodes the amino acid sequence of the fusion protein, with the DNA encoding the peptide substrate in the same reading frame as the DNA encoding the candidate protein.

The peptide substrate may reside either at the amino or carboxy termini of the candidate protein, or may be internal to the protein, for example, as a loop out of the candidate protein structure. Preferably, the peptide substrate is fused at the amino or carboxy terminus of the candidate protein.

According to the invention 'enzymatic modification' includes any modification of the peptide substrate which can be detected, for example by the binding of a marker or label, the addition or deletion of a chemical moiety from the peptide, a change of a chemical state such as phosphorylation, methylation, acetylation, ubiquitination, sumoylation, myristoylation or glycosylation. For example, with appropriate design of the peptide substrate, the change imposed by the modifying enzyme could activate the expression of an antibiotic resistance gene, allowing selection with antibiotics for the successful candidate, or activate the expression of a phenotypic marker gene, such as a gene encoding green fluorescent protein or beta-galactosidase, permitting a physical enrichment method such as FACS (fluorescent activated cell sorting). Preferably, the peptide substrate is biotinylated by enzymatic action. Other suitable types of modification will be clear to the skilled reader.

In an alternative embodiment, the peptide substrate may in some way affect the activity of the substrate modifying protein, for example, by acting as a co-factor for the enzymatic reaction, such that the activity of the substrate modifying protein is either raised or lowered specifically as a result of the solubility of the candidate protein. In this manner, if the candidate molecule expressed is soluble, the particular cell that encoded that candidate molecule may be isolated on the basis of the activity or inactivity of the substrate modifying protein, for example the complementation of an inactive mutant enzyme by a protein bearing a peptide that alleviates the effect of the mutation.

In the case of the preferred peptides for use in accordance with the invention, that are substrates for biotin protein ligase, the enzymatic modification is a change in the biotinylation state of the peptide.

In order for the enzymatic modification to take place, the presence of an enzyme is required that is capable of carrying out the required modification reaction. The enzyme may be added separately to the reaction mixture, or it may be endogenous to the reaction system, for example, being naturally expressed in a host cell in which the screening method is being carried out. For example, the cell may constitutively express the protein with activity as a substrate modifying enzyme. In an alternative embodiment, the host cell may be transformed with an extrachromosomal element such as a plasmid, episome, artificial chromosome or the like, containing the polynucleotide sequence encoding the peptide substrate modifying enzyme.

According to the invention 'detection' refers to any suitable method that allows the identification of enzymatic modification of the peptide substrate has taken place. Once altered by an enzyme, the peptide tag must differ in some respect to allow its discrimination from unaltered peptide substrate. In this manner, soluble candidate proteins can be distinguished from insoluble candidate proteins. Suitable methods for the detection of modified peptide substrate will be clear to those of skill in the art and will, of course, depend on the property of the modifying enzyme that is being utilised. Detection may either be for altered peptide substrate, or unaltered peptide substrate. Preferably, detection is a positive detection for altered peptide substrate. For example, in the preferred embodiment of the invention that utilises a peptide substrate whose biotinylation state is altered, selection may be for this change in biotinylation state, and may exploit the high binding affinity exhibited by avidin and streptavidin for biotin, to allow detection on the basis of the high binding affinity of this binding pair. Alternatively, mass spectrometry can provide a method of detection of tag modification by monitoring a change in mass. With this detection method, no binding partner is required The screening of the candidate proteins of the invention may be carried out in vitro, using for example a cell-free translation system in which the candidate proteins are transcribed and translated without being expressed in cells. In this scenario, there must be some linkage between genotype and phenotype so that selection of soluble candidate proteins allows the concomitant selection of the encoding nucleic acid. This allows the deconvolution of the methodology so that the advantageous sequence features that led to the production of soluble protein can be assessed. Suitable methods are known in the art. For example, one in vitro system recently published in International patent application WO99/02671 reports the use of microcapsules created using water-in-oil emulsions to compartmentalise and thus isolate the components of a translation system.

Preferably, the candidate proteins are expressed in host cells. As the skilled reader will appreciate, any host cell system in which the candidate proteins are expressed will be suitable, including prokaryotic expression systems such as streptococci, staphylococci, *E. coli, Streptomyces* and *Bacillus subtilis* cells, and eukaryotic systems such as yeast (for example, *S. cerevisiae* and *Aspergillus* cells), insect cells, plant cells and mammalian cell cultures. *E. coli* is a preferred host cell for use in accordance with the invention, in part because it expresses an endogenous biotin protein ligase that thus allows modification of peptide substrates fused to candidate proteins within the host cell itself. One advantage of this mechanism is that the required link between genotype and phenotype is maintained within each cell and so the method allows analysis of the DNA sequence of candidate proteins found to be soluble. Other host cells that do not express biotin protein ligase compatible with this particular peptide can also be used, however, by introduction of the coding sequence for the enzyme into the cells before screening.

For expression in host cells, nucleic acid sequences encoding candidate proteins, optionally as fusion proteins with the peptide substrate, should be cloned into a suitable vector or vectors. The host cells may be transformed, transfected or transduced with such vectors to effect expression of the candidate proteins to be screened. Suitable expression methods are well known to those of skill in the art and many are described in detail by Sambrook et al. (supra) and Fernandez & Hoeffler (1998, eds. "Gene expression systems. Using nature for the art of expression". Academic Press, San Diego, London, Boston, New York, Sydney, Tokyo, Toronto). Generally, the encoding gene is placed under the control of a control element such as a promoter, ribosome binding site (for bacterial expression) and, optionally, an operator, so that the DNA sequence encoding the desired polypeptide is transcribed into RNA in the transformed host cell. The encoding nucleic acid molecule may include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the polypeptide or they may be heterologous signals. Leader sequences can be removed by the bacterial host in post-translational processing. Preferably, the candidate protein is present in the same compartment of the cell as the substrate-modifying enzyme. For example, biotin protein ligase is a cytoplasmic protein and candidate proteins which are potential substrates for this enzyme should thus be retained in the cytoplasm. In addition to control sequences, it may be desirable to add regulatory sequences that allow for regulation of the expression of the polypeptide relative to the growth of the host cell.

The candidate protein can be recovered and purified from recombinant cell cultures for analysis, for example using well-known methods such as ammonium sulphate or ethanol precipitation, acid extraction and chromatography. However, some method must be used to allow the derivation of the recovered protein to be traced in order to retain the link between phenotype and genotype. More simply, the cells in which the candidate proteins are expressed may be lysed and analysed for modification of the peptide substrate. By recording the history of the colony from which a soluble candidate protein is derived retains the necessary link between genotype and phenotype. For example, in embodiments of the invention that screen for expression of soluble candidate proteins in host cells, the host cells can simply be lysed in situ on nitrocellulose membrane and tested for modification of the peptide substrate, for example, by blotting using antibodies, streptavidin or other detection reagents that recognise modified peptide substrate.

Specialised vector constructions may also be used to facilitate purification of proteins, as desired, by joining sequences encoding the polypeptides of the invention to a nucleotide sequence encoding a polypeptide domain that will facilitate purification of soluble proteins. Examples of such purification-facilitating domains include metal chelating peptides such as hexahistidine tags and histidine-tryptophan modules that allow purification on immobilised metals, protein A domains that allow purification on immobilised immunoglobulin, and the domain utilised in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and the candidate protein may be used to facilitate purification. The biotinylated protein produced by biotin protein ligase may also be purified using avidin-derivatised agarose.

The vector can also include a functional selection marker. The functional selection marker can be, for example, a resistance gene such as kanamycin, ampicillin, blasticidin, carbenicillin, tetracycline, or chloramphenicol. The vector further can include a dysfunctional selection marker that lacks a critical element, and wherein the critical element is supplied by a nucleic acid element upon successful transformation of the cell with that element. The dysfunctional selection marker can be, for example, a resistance gene or a reporter gene, such as the lacZ gene, and the like.

These possible arrangements may, of course, be mixed so that some of the components of the reaction system are expressed from the genome of the organism and some are expressed from an extrachromosomal element, such as an expression vector.

In order to improve the chances of successfully selecting for soluble candidate protein, the reaction system should be incubated under conditions that are suitable for the activity of the peptide substrate-modifying protein. For example, in the case where an exogenous substrate modifying protein is added to a reaction medium, this medium should be placed under conditions suitable for the activity of the added protein. In cases where substrate-modifying protein is expressed in a host cell that is used in the screening methodology, the host cells should be grown under conditions suitable for their healthy growth and for the activity of the expressed protein. In such cases, there should be present in the system the appropriate transcriptional and translational machinery to allow expression of the substrate modifying protein from its encoding gene(s). This machinery will in most cases be derived from the cell itself.

The method allows the screening of a plurality of candidate protein variants. Indeed, one strength of the method is that it allows a very large number of different variants to be screened in parallel for activity. This means that it is possible, if desired, to perform an exhaustive screen for all or a very large number of possible variants of a particular protein or proteins, since the method is amenable to high throughput analysis.

Methods for the creation of libraries suitable for use in the above-referenced aspects of the invention are well known in the art. For example, one way to effect truncations of this type is to use the various well-known techniques of genetic engineering to delete selectively the encoding nucleic acid sequence at either or both ends, and then insert the desired coding sequence into the vector of choice. For example, to identify a particular soluble variant for a protein that has proven difficult to solubilise, a library of truncations may be made. Such a library may contain progressive single or multiple amino acid truncations at either or both the N terminal and C terminal ends of the protein.

PCR amplification of the target gene using random primers can be used to generate gene fragments truncated at both ends (Kawasaki et al, Random PCR-based screening for soluble proteins using green fluorescent protein, *Biochem. & Biophys. Res. Comm.* 2001 vol 280 pp 842-844). Other equivalent methods include generating DNA fragments by various enzymatic methods (e.g. using uracil deglycosylase or DNAseI) or physical methods (e.g. sonication, point-sink shearing). However, some of these endonuclease or "nicking" methods are biased in their "cut sites" (e.g. uracil deglycosylase & DNAseI) so that not all fragments are represented. Furthermore, methods of physical fragmentation (e.g. sonication, point-sink shearing) generates damaged DNA ends that must be repaired with an enzymatic step prior to cloning. This can result in a low cloning efficiency.

Both these fragmentation methods generate inserts that must be cloned into a vector backbone using a 2-part ligation, but this is significantly less efficient than a 1-part ligation due to the lower probability of molecular collision.

In order to overcome the disadvantages associated with truncation methods known in the prior art, attempts have been made to generate incremental truncation libraries in which one end of the candidate protein is fixed and the other end varies. For example, the C terminus may be fixed and the N terminus varied, or the N terminus fixed and the C terminus varied. As an example of such a strategy, for a 770 amino acid protein, there are 670 truncations that leave a protein of greater than 100 amino acids in length (the approximate practical lower size limit for proteins expressed and screened in *E. coli*). At the DNA level, this corresponds to 2010 nucleotides. An over-sample of 10-fold will necessitate the construction and screening of 20,100 clones. One third of these clones will be in frame whilst two thirds will contain a frameshift and therefore not express a useful peptide-tagged protein.

However, although such methods partially overcome the disadvantages associated with the methods known in the prior art, they are far from ideal. For example, the cloning of randomly fragmented DNA molecules generated by enzymes or physical breakage suffers from the disadvantage that for a particular protein of "N" residues, approximately $N^2/2$ fragments will exist. The DNA insert normally has a one in three chance of being in the correct reading frame at each end and can insert in one of two orientations. In order to ensure that the protein coding sequence is in the correct orientation and in-frame at both ends requires an 18-fold over-sampling. Taking the example of a gene encoding a 500 amino acid protein, this yields 2 million possible ligation products; a 10-fold over-sample thus means that a library of 20 million clones must be sampled. Even with the advent of high throughput screening methods, screening 20 million clones represents a significant research project. In contrast, unidirectional truncation strategies reduce the diversity of the DNA fragments to N (where N is the number of nucleotides in the gene) and this is a much more manageable number. In some cases this may yield soluble protein fragments, but has the drawback that one end must remain fixed meaning that internal domains, independent of the ends, cannot be isolated.

Despite these drawbacks, such methods are used. For example, unidirectional truncation has now become a well-established method and has been used to generate inserts for expression analysis (Cornvik et al., PROTEINS: Structure, Function, and Bioinformatics 65:266-273 (2006); Cornvik et al., Nature Methods, 2(7); 507 (2005)).

The inventors have surprisingly now found that by introducing two unidirectional cleavage sites in a vector containing a nucleic acid insert of interest, one at either end of the nucleic acid insert, a stepwise process can be used to truncate both the 5' and 3' of the insert whilst maintaining its correct orientation.

The invention relies on the use of cleavage steps, preferably using restriction enzyme digestion, combined with controlled or random exonuclease digestion of nucleic acids. The bi-directional method comprises two sequential steps of plasmid linearisation, digestion of one end, and recircularisation.

The method works using a vector that comprises two pairs of restriction sites, positioned in the vector so as to flank the nucleic acid insert which it is desired to truncate. In a first step, the vector is digested with a first pair of restriction enzymes such that an exonuclease-susceptible nucleic acid end results on the insert side of the vector and an exonuclease-resistant end results on the vector side. The insert is then digested using a standard exonuclease procedure and the vector then recircularised by ligation. In the ensuing step, the resulting plasmids are again digested with the second pair of restriction enzymes, again, such that an exonuclease-susceptible nucleic acid end results on the insert side of the vector and an exonuclease-resistant end results on the vector side. The vector is then again recircularised by ligation.

Accordingly, this aspect of the present invention provides a method of generating a library of nucleic acid molecules of varying sizes, wherein each nucleic acid molecule forms an insert within a vector, and each vector comprises two pairs of restriction enzyme cleavage sites positioned so as to flank the nucleic acid insert, the method comprising:

a) cleaving a plurality of vectors with a first pair of restriction enzymes such that an exonuclease-susceptible nucleic acid end results on the insert end of the vectors and an exonuclease-resistant end results on the vector end;

b) digesting the linearised vectors using an exonuclease, followed by removal of single-stranded DNA;

c) recircularising the vectors by ligation;

d) cleaving the recircularised vectors with a second pair of restriction enzymes which cleave at the cleavage sites positioned in the vector on the other flank of the nucleic acid insert, such that an exonuclease-susceptible nucleic acid end results on the insert end of the vectors and an exonuclease-resistant end results on the vector end; and e) digesting the linearised vectors using an exonuclease, followed by removal of single-stranded DNA; and f) recircularising the vectors by ligation.

By performing this methodology repeatedly, perhaps by taking samples at different time points of exonuclease digestion or by inactivating samples at different time points of exonuclease progression, a library of nucleic acid inserts may be generated.

The vector, containing a mix of gene inserts truncated at both ends can, for example, be electrophoresed on an agarose or polyacrylamide gel and the size range of interest (e.g. plasmids with inserts of 900 bp to 1500 bp) cut from the gel. These plasmids can then be transformed into a suitable host strain (e.g *E. coli*) for downstream analysis e.g. protein expression testing.

This aspect of the invention thus provides a method for generating a library of correctly oriented, random nucleic acid fragments. These may advantageously be used for any application required, for example, for protein expression trials along the lines described above, or in any other application where one nucleic acid orientation is preferred over the other. The method of this aspect of the invention is particularly well suited to the generation of a library of nucleic acid molecules which code for truncated protein variants, to be screened for solubility according to the aspects of the invention described above, herein.

This method has the advantage that it is capable of generating an internal fragment library, whilst overcoming the necessity for an 18-fold over-sampling as required by the methods disclosed in the prior art. Due to being able to maintain the correct orientation of the insert of interest throughout the truncation procedures, the method of generating a truncated insert library as disclosed herein in is at least 100% more efficient than those methods for creating internal fragment libraries that are disclosed in the prior art.

The method disclosed herein provides the further advantage that all ligation steps are carried as unimolecular ligations and, therefore, there efficiency is greatly increased compared to standard "insert+vector" ligations. One-part ligation reactions are very much more efficient (perhaps 100× more colonies per μg of DNA), and therefore it is simpler to obtain large numbers of cloned DNA inserts.

The method of this aspect of the invention also allows for sampling of fragments that are uniformly distributed along the length of the insert of interest. The preferred processive enzyme, Exonuclease III, digests processively from either end of the insert and is unbiased, meaning that all end combinations can be generated. Because the method of this aspect of the invention allows all end combinations to be generated, it is possible to generate constructs of proteins which were previously thought to be "impossible" to express. This is due in part to the fact that single amino acid differences at the N- and C-termini of proteins can sometimes have a large effect on yield, solubility and stability of the any given construct. As the method potentially allows for the generation and screening of all possible combinations, the optimum construct for yield, solubility and/or stability can be generated.

The method of this aspect of the invention is also advantageous over bioinformatic construct prediction. A clear understanding of the specific factors which affect a particular construct's yield, solubility and/or stability is still many years away and, therefore, bioinformatic methods suffer from a degree of uncertainty. The same uncertainty is not a concern for the method of the present invention and, indeed, is not even a consideration in view of the essentially random methods by which constructs are generated.

Additionally, these fragments can be selected with certain size ranges to increase the efficiency of sampling diversity. Furthermore the methods can be adapted so that the difference in size between the inserts of interest in each member of the truncation library can be 1, 2, 3, 4, 5, 6, 8, 10, 12, 15, 20, 25, 30, 40, 50 or more nucleotides, depending on the requirements of the experiment being conducted. A preferred method for size selection is using gel electrophoresis, and subsequent excision of relevant nucleic acid bands.

The invention combines the specific substrate requirements of the exonucleases with the specific substrate requirements and cleavage patterns of known restriction enzymes. For example, certain restriction enzymes cut at sites that leave 3' overhangs (e.g. NsiI). Others cut at sites that leave 5' overhangs (e.g. NotI). By cutting at one or the other of these sites, then using either 3' and/or 5' exonuclease enzymes and incubating the reaction for controlled periods of time, a selective degree and direction of digestion can be achieved.

Examples of vector constructions that are suitable for use with the method of the present invention are described above, and in the Examples contained herein. Preferably, the vector used is a plasmid vector.

Examples of nucleic acid inserts of interest are random DNA fragments, DNA fragments that are candidate consensus sequences (such as potential protein binding sites, promoter or enhancer sequences), nucleic acid fragments that are putative drug compounds, DNA fragments that encode RNA (for instance, RNAi), and DNA fragments that encode protein domains or partial protein domains (either for structural determination, for domain mapping, for determination of consensus sites, for analysis of activity and so on), DNA fragments that encode antibody domains (e.g. Fab, scFv, Fc domains, CDRs etc.) and DNA fragments that encode peptides. The term "insert" as used herein is thus intended to embrace nucleic acid molecules of these varied forms, including DNA molecules of unknown function as well as entire genes or longer sequences, perhaps even chromosomes. For example, where the libraries of the invention are used as a tool to determine a DNA binding site, the gene maybe a stretch of DNA suspected of containing a particular DNA binding site.

The method of generating a truncated gene library envisaged by this aspect of the invention relies upon a vector comprising an insert of interest and two unidirectional cleavage sites, wherein one unidirectional cleavage site flanks the 5' end of the positive sense strand of the insert and the other unidirectional cleavage site flanks the 3' end of the insert.

The method comprises digesting the vector with a first pair of restriction enzymes which act on one of the unidirectional cleavage sites. Cleavage by both of these enzymes results in a linearised plasmid in which the insert has an overhang which acts as a substrate for an exonuclease, whilst the vector is not capable of acting as a substrate for the same exonuclease.

Examples of suitable pairs of restriction enzymes will be known to those of skill in the art, given the requirement that the restriction site on the insert side of the vector must on cleavage provide an overhang that is susceptible to exonuclease digestion, and that the restriction site on the vector side distal to the insert must on cleavage provide an overhang that is resistant to exonuclease cleavage. Examples of suitable restriction enzyme pairs include AatII & AscI; and NsiI & NotI).

Once linearised, the vector is exposed to the exonuclease under conditions which allow exonuclease activity to take place. Suitable conditions will be known to those of skill in the art.

The term "exonuclease" includes any enzyme capable of degrading either the 3' and 5' termini of duplex DNA. Such enzymes include proofreading polymerases, exonuclease I-X and Bal-31. Preferably the exonuclease used in the method of this aspect of the invention is exonuclease III (ExoIII). ExoIII degrades dsDNA from blunt ends and from 5'-overhangs or nicks, releasing 5'-mononucleotides from the 3'-ends of DNA strands and producing stretches of single-stranded DNA. It is not active on 3'-protruding ends of DNA that are at least one base long; on single-stranded DNA, or on phosphorothioate-linked nucleotides.

To obtain a variety of different insert lengths, the exonuclease reaction should be curtailed at various time points. The reaction may be stopped by any suitable means, either by quenching the entire reaction or by removing samples at various time points. For example, the reaction may be heated to denature the enzyme, or the pH or salt concentration of the reaction may be altered such that the exonuclease will become inactive.

The linearised vectors resulting from the various exonuclease reaction time points are preferably exposed to conditions where any single stranded DNA present in the linearised vector is removed. This may be achieved by any means known in the art. Preferably the ssDNA is removed enzymatically. More preferably the ssDNA is removed by mung bean nuclease or S1 nuclease.

Once the ssDNA has been removed from the vectors they are religated so as to be recircularised. Optionally, before the ligation, the linearised plasmids may be subjected to a "polishing step". The polishing step involves ensuring that both ends of the plasmid are blunt. This can be achieved by exposing the linearised plasmid to any DNA polymerase having a proof-reading activity. Preferred examples are Klenow fragment, T4 DNA polymerase, PWO polymerase or Pfu polymerase.

Preferably, a size selection step is included between the exonuclease digestion and the religation of the plasmids. The size selection step involves selecting clones based on the size of the insert. The clones can then be split into multiple sub-libraries, for example with an insert size of 0-1 kb, 1-2 kb and 2-3 kb. Separation of the clones into sublibraries in this way has the advantage of preventing small clone domination and allows a more evenly distributed sample of the insert to be obtained. The size selection step is preferably carried out after the polishing step, but may also be carried out in between the ssDNA removal and polishing step. The size selection step may be achieved using any means known in the art. For example, the linearised plasmids may be purified using size exclusion liquid chromatography. Preferably, the linearised plasmids are separated on an agarose gel using techniques well known in the art. The band(s) of interest are then excised from the gel and the DNA extracted.

The resulting circularised vectors may then be amplified. The amplification may involve transforming a suitable host cell strain with the vectors, growing the transformed cells and purifying the vectors from the resultant cell population.

As the skilled person will appreciate, each time point sampled will result in a vector with a different sequence. If, for example, time points are taken every 30 seconds for an hour, then the sample taken at t=30 secs will have more of the gene of interest present than the sample taken at t=1 minute. The number of samples taken at different time points of steps may be very varied, and for example may be 2, 3, 4, 5, 10, 15, 20, 25, 30, 35, 40, 45, 50, 55, 60, 65, 70, 75, 80, 85, 90, 95, 100, 115, 130, 145, 160, 175, 190, 205, 220, or more. The samples may, for example, be taken at time points separated by 5, 10, 15, 20, 25, 30, 45, 60, 90, 120, 180, 300, 450 or more seconds.

Each of the different vectors produced in the first stage of the method are treated as individual vectors in the second stage. That is to say, that the second stage of the method, as described below, is carried out on each of the vectors produced in the first stage.

The second stage of the method comprises digesting the vector with a second pair of restriction enzymes which act on the unidirectional cleavage site which was not cleaved in the first reaction. Cleavage by this pair of enzymes results in a linearised vector which has one end, the insert end, capable of acting as a substrate for an exonuclease, whilst the other end, the vector end, is not capable of acting as a substrate for the exonuclease.

As with the first stage of the reaction, once linearised, the vector is exposed to the exonuclease under conditions which allow exonuclease activity. Samples of the exonuclease reaction are preferably taken at more than one time point and the exonuclease reaction is stopped. The linearised vectors resulting from the various exonuclease reaction time points are preferably exposed to conditions where any single stranded DNA present in the linearised vector is removed. Once the ssDNA has been removed from the vectors they are religated so as to be recircularised. Optionally, before the ligation, the linearised vectors may be subjected to a "polishing step".

The method according to this aspect of the invention may comprise the additional step of amplifying the recircularised vectors.

A nucleic acid "end" as used herein, refers to a specific end of a linearised vector. If the vector contains a DNA insert of interest and is cleaved at either the 5' or 3' of that gene then on one side of the cleavage site will lie the insert sequence, whilst on the other will be the vector sequence.

The term "vector" as used herein refers to both a single copy of a vector and multiple copies of a vector. Where the term refers to multiple copies of a vector, each copy may share the same sequence or each copy may have a sequence which differs. If the vectors differ in sequence, they may be 99, 98, 97, 96, 95, 94, 93, 92, 91, 90, 85, 80, 75, 70, 65, 60, 55, 50, 45, 40, 35, 30, 25, 20, 15 or 10% homologous. For example, if multiple copies of the same vector are linearised and exposed to an exonuclease reaction for varying periods of time and then religated the resulting vectors will differ in sequence.

Preferably, the restriction enzyme cleavage results in the insert end of the linearised vector having a 5'-overhang and the vector end having a 3'-overhang. The choice of whether the insert end or vector end is left with a 5' or 3'-overhang is of course dependent on the choice of exonuclease. Preferably, the gene end of the linearised vector will always have an overhang which acts as a substrate for the particular exonuclease chosen.

Preferably the method of generating the library further comprises the additional step of transforming a suitable host cell with the vectors produced in the reaction to produce a library of nucleic acid inserts. This additional step may involve transforming a suitable host cell with the vectors, growing the transformed cells and purifying the vectors from the resultant cell population. Methods for carrying out each of these steps are common practice in the art.

As will be appreciated by the skilled person, certain bacterial strains are more amenable to transformation and subsequent amplification of the vector, whilst other vectors are more amenable for protein expression. Where the invention refers to transformation of a suitable host cell, this term "transformation" includes multi-step transformations. For example, the vectors may first be used to transform a strain of bacteria useful for vector amplification, e.g. DH5a. Once amplified the vector of interest may then be extracted from the DH5a strain and used to transform a strain of bacteria useful for expression, e.g. BL21. Various strains of cells useful in the methods of the invention are envisaged. These preferably include prokaryotic cell lines such as DH5a, BL21, but may also include eukaryotic cell lines such as yeast, insect or mammalian cells.

Preferably, different cells of the library of nucleic acid insert clones express different candidate proteins.

The term "unidirectional cleavage site" refers to a short stretch of DNA sequence which is cleavable by a pair of restriction enzymes. The first restriction enzyme of the pair is selected to generate a 3'-overhang upon cleavage, whilst the second restriction enzyme is selected to generate a 5'-overhang upon cleavage. The first restriction enzyme may be, but is not limited to, AatII, ApaI, BanII, BglI, BsfXI, HaeII, KpnI, NsiI, PstI, SacI or SphI.

Preferably the first restriction enzyme can be AatII or NsiI. The second restriction enzyme may be, but is not limited to AscI, BamHI, ClaI, Csp45I, EcoRI, EcoRV, HindIII, NcoI, NdeI, NotI, SalI, SmaI, SpeI, XbaI or XhoI. Preferably, the second restriction enzyme can be AscI or NotI.

This aspect of the invention also includes a library of nucleic acid inserts generated by the method of this aspect of the invention.

The term "bidirectional truncation" as used herein, refers to a nucleic acid molecule which has been truncated from its starting sequence at both the 5' and 3' end.

The term "time points" as used herein refers to the time period taken from the start of a reaction until the reaction is ended. For example, a reaction initiated at t=0 may be carried out for 30 seconds and stopped at that point, i.e. the reaction is stopped at t=30 secs. Therefore, t=30 secs is a time point in the sense of the present invention. The methodology of the present invention generally relies upon samples taken at multiple time points, preferably from a single reaction mixture. For example, a reaction may be initiated and small samples removed from the starting volume at specified time points. The reaction in each of these samples can then be stopped at a range of time points. For example, samples may be taken every 5, 10, 15, 20, 25, 30, 45, 60, 90, 120, 180, 300, 450, 600, or more seconds. The number of samples taken may also be varied. For example, 2, 3, 4, 5, 10, 15, 20, 25, 30, 35, 40, 45, 50, 55, 60, 65, 70, 75, 80, 85, 90, 95, 100, 115, 130, 145, 160, 175, 190, 205, 220, or more samples may be taken. The skilled reader will appreciate that any length of time point can be combined with any number of samples. It will also be appreciated that although it is preferred to initiate a reaction in a single large starting volume and take samples at a range of time points, it is also possible to run multiple small reactions for the same time periods as covered by sampling the large initial volume, and stop each reaction at some specified time. For example ten small reactions may be run, wherein reaction one is stopped after 30 secs, reaction 2 after 60 secs, reaction 3 after 90 secs, and so on.

In a preferred embodiment, a large number (e.g. 50%, 60%, 70%, 80%, 90%, 95% or more), or even all possible truncations of the coding sequence of a protein are made and tested. In order to be reasonably confident that an exhaustive screen has been performed, it will be necessary to over-sample each truncation by at least 3-fold, preferably at least 5-fold, more preferably 10-fold. However, even low sampling of perhaps 1% of the clones can provide useful constructs The truncation libraries generated by the methods described above are useful in the methods of screening for soluble candidate proteins as disclosed herein. However, it will also be clear to the skilled person that both the methods, and the truncation libraries, as described above, provide a useful tool in may areas of molecular biology.

In the particular embodiment of the invention which screens for soluble protein fragments, a peptide substrate that is susceptible to enzymatic modification when soluble (e.g. biotin) is preferably expressed as a genetic fusion with the encoded protein fragment, forming a recombinant fusion protein. The attachment of the peptide substrate and the candidate protein components may be achieved using a recombinant DNA construct that encodes the amino acid sequence of the fusion protein, with the DNA encoding the peptide substrate in the same reading frame as the DNA encoding the candidate protein. The peptide substrate preferably resides either at the amino or carboxy terminus of the candidate protein.

As above, specialised vector constructions may also be used to facilitate purification of proteins, as desired, by joining sequences encoding the polypeptides encoded by the invention to a nucleotide sequence encoding a polypeptide domain that will facilitate purification of soluble proteins. Examples of such purification facilitating domains include metal chelating peptides such as hexahistidine tags and histidine tryptophan modules that allow purification on immobilised metals, protein A domains that allow purification on immobilised immunoglobulin, and the domain utilised in the FLAGS extension/affinity purification system (Immunex Corp., Seattle, Wash.). The presence of, for example, a hexahistidine tag permits rapid verification of solubility via a small-scale metal affinity chromatography column and secondly permits direct scale-up and purification of the truncated proteins. The inclusion of cleavable linker sequences such as those specific for Factor XA or enterokinase (Invitrogen, San Diego, Calif.) between the purification domain and the candidate protein may be used to facilitate purification. The biotinylated protein produced by biotin protein ligase may also be purified using avidin-derivatised agarose.

The inclusion of an N-terminal tag confers the further advantage that the tag permits parallel screening on the same membrane. For example, the presence of a N-terminal hexahistidine tag permits parallel screening on the same membranes for the intact N-terminus of the protein using an antibody with a fluorescent dye (perhaps via a secondary, generic dye-labelled antibody). Thus colonies yielding a signal from the streptavidin hybridisation indicate that the protein is soluble and the presence of a histidine tag signal indicates that the protein is full-length. In this way, false positives resulting from internal initiation of translation within the gene, or premature termination of translation, may be simply screened out since presence of both ends of the protein indicates that it is full-length. Additionally, In suitable vectors for use in this aspect of the invention, the coding sequences for the peptide substrate, and/or purification tag should be on the vector side of the unidirectional restriction enzyme cleavage sites, such that the processive truncation of the nucleic acid insert occurs only within the insert sequence. Accordingly, when the vector is recircularised, these coding sequences remain intact and positioned so as to flank the nucleic acid insert.

A preferred vector construction utilises a hexahistidine tag at one terminus of the candidate soluble protein and a biotin peptide tag at the other.

Alternative High Throughput Screens for Detecting Soluble Proteins

The use of the truncation libraries as disclosed is not limited to the methods for determining protein solubility as described herein. The truncation libraries may be used upstream of any method, preferably any high throughput method, for determining protein solubility. Examples of such methods include ESPRIT (see the methodology of co-pending International patent application PCT/GB2005/003417), the so-called CoFi blot (Cornvik et al., Proteins: Structure, Function and Bioinformatics, 2006, 65:266; Cornvik et al., Nature Methods, 2005, 2:507), GFP fusions or short fragments of GFP or other fluorescent proteins, fusion of chloramphenicol acetyl transferase, bleomycin resistance protein, kanamycin resistance protein (or any other antibiotic resistance proteins), filtration either in a multiwell filter plate format (FiDo method) or in colony format (CoFi method), or purification on Nickel NTA resin in multiwell format.

As described above, because the orientation of the gene of interest is always maintained, the method is at least 100% more efficient than the methods of producing internal fragment libraries known in the prior art.

Crystallisable Domains.

The truncated gene libraries of the invention are useful in structural biology studies. In order for X-ray structure determination techniques to be applied to a protein, high-quality crystals of the protein must be grown. Acquiring a variant of the protein, which is both soluble and capable of being expressed in milligram quantities is only the first step in this process.

A clear understanding of the specific factors which affect a protein's ability to crystallise is still many years away. Therefore, the initial route for obtaining protein crystals suitable for X-ray studies is the screening of one soluble protein variant against a large number of crystallisation conditions, for example, using those screens available from Hampton research (hamptonresearch.com). In many cases, the particular protein variant being tested is not amenable to crystallisation and further protein variants must be tested before suitable crystals are obtained.

The advent of robots capable of setting up large numbers of crystallisation screens simultaneously has meant that the rate limiting step in many cases is now the production of protein variants which are soluble and suitable for crystallisation trials. The truncated gene libraries of the present invention circumvent this problem and allow the production of a large number of soluble protein truncations that can be tested for the ability to form crystals.

Protein Functional Domain Mapping

The methods for producing truncation libraries as disclosed herein facilitate investigations into protein function. For example, the libraries can be used to express all of the possible fragments of a protein. These fragments can then be assayed for particular functions. For example specific protein domains, such as zinc finger binding domains can be excised from larger proteins. Proteins belonging to pathogenic organisms can be assayed for immunogenic potential for vaccine, anti-viral, anti-fungal and anti-microbial production. Furthermore, protein fragments produced could be used as detection moieties in biosensors.

DNA Binding Domain Mapping

The truncated gene libraries disclosed herein are also of is in determining the function of DNA. For example, the gene of interest used in the vector of the method may be a DNA sequence known to contain a promoter and/or a transcription factor binding site. Using the methods disclosed herein, every possible fragment covering the span of DNA in the original vector could be tested for the presence of the promoter/transcription factor. The precise identity of the DNA sequence of interest can then be elucidated. The skilled person will appreciate that the same technique could be applied to any specific sequence of interest contained within a larger DNA sequence.

RNA Mapping

The method of the invention is applicable to any scenario in which the generation of a number of variants of a nucleic acid sequence is desired. One application is thus the generation of varied coding sequences for RNA molecules, such as RNAi.

Combinatorial Library Methods

The method of this aspect of the invention can also be combined with other methods known in the art to increase their utility. For example, gene constructs produced using "directed evolution" techniques can then subjected to the method of the invention. Such a combination would allow the high throughput screening of all fragments from a large number of possible protein variants.

Mutagenesis

A library of variants may be generated in which mutations have been made. Mutagenesis may be random mutagenesis, or may be rational, site-directed mutagenesis. Suitable methods of manipulation will be known to those of skill in the art and include point mutagenesis (error-prone PCR, chemical mutagenesis, the use of specific mutator host strains), recursive ensemble mutagenesis (Delagrave and Youvan (1993) Bio-Technology, 11: 1548-1552), combinatorial cassette mutagenesis (Black et al., 1996), DNA shuffling (Stemmer et al., 1994) or by codon substitution mutagenesis. For a review of recent improvements in processes for in vitro recombination, see Giver and Arnold, 1998 (*Current Opinion in Chemical Biology*, 2(3): 335-338). For example, a particular amino acid or acids might be selectively mutated from the wild type sequence to other amino acids. Such mutants may include variant candidate proteins in which one or more of the amino acid residues are substituted with a conserved or non-conserved amino acid residue (preferably a conserved amino acid residue). For example, residues of high conformational flexibility such as Arg or Lys might be exchanged for those of low entropy such as Ala with the aim of improving the homogeneity of crystallisation in order to achieve better quality protein crystals for X-ray analysis. Such substituted amino acid residue may or may not be one encoded by the genetic code. Typical such substitutions are among Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 5 and 10, 1 and 5, 1 and 3, 1 and 2 or just 1 amino acids are substituted, deleted or added in any combination. Especially preferred are substitutions, additions and deletions which do not alter the functional properties or activities of the protein. Also especially preferred in this regard are conservative substitutions. Such mutants also include polypeptides in which one or more of the amino acid residues includes a substituent group.

A library of variants may be made in which insertions have been added to the sequence, for example, of one or more amino acids, or a run of amino acids so as, for example, to form or delete a loop in the candidate protein. Particularly if hydrophilic amino acids are included, an enhancement of the solubility of the candidate protein may result.

These libraries of candidate proteins are then screened for the particular variant(s) that exhibit the greatest degree of solubility.

According to this aspect of the invention, a library of candidate proteins may contain more than $10^3$ different clones, more than $10^4$ different clones, more than $10^5$ different clones, more than $10^6$ clones, more than $10^7$ clones, more than $10^8$ clones or even more. Preferably, the library is sufficiently large in size to contain clones expressing every possible truncation and variant of the candidate protein. This is advantageous because the creation and testing of all possible truncations greatly increases the chances of success and allows for the analysis of large amounts of data which can be used to link variations in solubility to features of the protein sequence. Furthermore, a comprehensive screen of all positions allows an experiment to be abandoned with confidence should only negative results be obtained.

A library of clones may comprise a plurality of transformed cells, each cell of which expresses a different candidate protein. Such a library can be created by transforming a preparation of cells with a library of suitable vectors. Under the appropriate conditions, transformation with such vectors may be performed so as to ensure that substantially only one type of candidate protein is expressed in each cell of the library. This confines the proteins that are expressed from that nucleic acid within the same cell and facilitates the selection of nucleic acids encoding molecules of interest; were each cell to include multiple nucleic acid molecules, then upon isolation of the cell it would not be clear which nucleic acid molecule had encoded the protein that caused the desired effect.

The improved selection techniques that form part of the invention permit the simple use of reiterative molecular evolution cycles so that large pools of potential candidates can be carried through a series of repetitions. Preferably, a clone expressing highly soluble candidate protein will be obtained from the library of clones without the need for any further manipulations. However, in order to optimise the solubility of a candidate protein that has been identified as soluble by the method of the invention, it may be necessary or desirable to perform reiterative steps of sequence alteration and screening. For example, the screening of an initial library may select a number of candidates with increased solubility, although this library will be predominantly contaminated with clones expressing insoluble or non stably-expressed protein. However, reiterative cycling, using soluble candidates selected after the first round of screening to parent a next generation of candidates allows the process to be repeated; it may be possible to evolve these soluble candidates further toward solubility by performing additional steps of sequence alteration and screening. The content of the pool will increasingly become populated by more soluble ("fitter") candidates. After a series of reiterative cycles, the pool of successful candidates can be taken and manipulated to create a new library that is used to start a new series of reiterative cycling under a more stringent selection criterion. Preferably, only one iteration of the manipulation and screening steps is performed, more preferably three, still more preferably four or more. The possibility of automation may allow the use of many more cycles, perhaps exceeding 100, 500 or 1000, if necessary.

In order to use the methodology of the current invention to its full potential in a high throughput screening methodology, it is necessary that the screen can function on a scale commensurate with the size of the library. To fully exploit the potential of this type of technology, the use of a colony picker and arraying robot should be used to convert plated transformants into an ordered library and screen these for positive colonies. Ideally, each colony is given an "address" that corresponds to a particular well in a plate. The use of barcodes can facilitate this. Optionally, the library can be replicated exactly for security.

Preferably, the screening and selection of colonies is automated, using video technology combined with a 96 pin picking head and the like. 384 well plates can accelerate the process by allowing more colonies to be screened. Using this technology, an approximate picking rate of 2500 colonies per hour is easily achieved.

In a preferred methodology for putting the method of the invention into effect, a library of transformants are arrayed as inocula onto nitrocellulose membranes over LB agar, resulting in colony arrays (Buessow et al, 1998 *Nucleic Acids Research* Vol 26, pp 5007-5008). Expression of the proteins is induced, for example, by shifting the membrane onto agar containing IPTG and biotin and growing the cells for around 3 hours at a suitable temperature. The cells are then lysed in situ. A large-scale dot blot analysis can then be performed for protein and/or DNA content. In this way, 60,000 clones can be arrayed and tested per 22×22 cm membrane. Using such an assay format has advantages over expression of clones in microtiter plates since the colonies themselves act as expression vessels and the logistics of expressing and testing so many clones are greatly simplified. If arranged in a readily deconvolutable geometric array, quantitation of expression levels and solubility levels is facilitated by use of array analysis software; clones can be ranked for expression level and prioritised. The method allows easy, parallel processing of large numbers of assay points and simple tracking of assay data back to the physical original clone. Such processing is preferably software-controlled.

In this type of methodology, cellular proteins from the arrayed colonies are deposited on the membrane after in situ cell lysis by placing the membrane with colonies on a sodium hydroxide-soaked pad. The proteins can be detected by an antibody against the tag which is insensitive to the post translational modification (e.g. biotinylation) and this permits assessment of protein yield although does not indicate the solubility status of the protein. More importantly, the protein can be detected using a detection method that is sensitive to the solubility status of the clone e.g. in the case of post-translational biotinylation of the protein indicating solubility, streptavidin binding provides a readout on whether the tag has been modified. Additionally, useful information on expression conditions can be achieved by comparison of the antibody and streptavidin signals, e.g. in an XY scatter graph, thereby permitting an estimation of the fraction of total protein that is soluble. If the streptavidin is conjugated to a peroxidase or alkaline phosphatase, the detection can be by chemiluminescence or conjugated to a fluorescent dye, visualisation can be by fluorescence imaging. Clones identified as biotin positive can then be isolated front the library and tested in conventional ways to verify soluble expression. Thus a clone exhibiting a biotin positive phenotype can be grown in liquid culture, protein expression induced by addition of IPTG and the solubility status confirmed by lysis and subsequent fractionation of the lysate into insoluble and soluble preparations e.g. by centrifugation or filtration. Proteins can then be analysed and characterised, such as by SDS-PAGE and western blot.

In an improvement that permits sensitive ranking of positive clones and therefore prioritisation of clones, the colony arrays are probed with fluorescent streptavidin e.g. labelled with Alexa488 dye. Detection may then be performed using a fluorescent imager such a Typhoon Imager (Amersham).

A comparison of replicate membranes probed with antibody and streptavidin thus permits a readout of the solubility status of a particular variant e.g. truncation, as being expressed or not expressed, soluble or insoluble. In this way an "expression map" can be generated permitting measurement of the effects of truncation at single amino acid resolution. This is the type of information that structural biologists require when designing constructs for protein expression and may lead to a deeper understanding of factors affecting protein expression.

In more detail, clones can be sequenced to identify the exact identity of the truncations and to identify junctions and replicates. Using these data, clones can be prioritised by expression level and size to from the information contained in a soluble expression map (FIG. 6) that correlates the solubility of the construct against the truncation point in the encoding gene sequence. As can be seen from FIG. 6, there is a degree of order evident from portraying the degree of solubility of the various clones ranked according to the sequence of the encoding gene. Similar levels of solubility are evident in constructs with consecutive truncations (see straight lines drawn through marker points), and these are believed to correspond to regions of consecutive residues in solvent-exposed linkers. In contrast, gaps of poor solubility are evident from truncation boundaries that fall within structured regions in the protein (see region marked as "binding domain" in FIG. 11). It is hypothesised herein that this type of analysis allows an exhaustive analysis of the solubility of truncated variants of a protein to divulge information on protein structure, such as domain boundaries, and the degree of solvent exposure of residues in the primary structure of the protein. Thus, in a further aspect, the invention provides a method for obtaining information relating to protein structure, the method comprising performing a method of screening according to any one of the embodiments of the invention described above, and correlating information regarding the solubility of each construct with the truncation point in the protein sequence. Preferably, the data obtained from the any one of the embodiments of the invention is used to create a soluble expression map by plotting the solubility of the construct against the truncation point in the encoding gene sequence. Solvent-exposed linker regions are identified as regions of consecutive residues with significant solubility. Gaps between solvent-exposed linker regions are identified as structured regions in the protein sequence. Inflexion points between the solvent-exposed residues and the structured regions are identified as domain boundaries within the protein sequence.

Prior to expression testing in the array format above, the quality of the gene truncation libraries should be measured by analysis of the distribution of sizes of gene fragments. Such characterisation will typically involve a PCR screen with primers that flank the insert. This gives an idea of the size of the insert. The start codon can then be confirmed by digesting the PCR product using a restriction enzyme that includes ATG in its recognition site (e.g. NdeI). Following expression-testing in the array format and isolation of positives from the library, clones can be sequenced to identify the exact identity of the truncations.

In conjunction with the methodology described above, suitable controls should preferably be used to ensure that false positive and false negative results are taken into account. For example, a positive control should use a protein that is known to be soluble under the conditions used for the screening. An example of a positive control might be maltose-binding protein (MBP) to which the peptide substrate is fused. This protein is solubly expressed and thus experiences modification of the peptide substrate by the substrate modifying protein. In the embodiment of the invention that utilises a biotinylation peptide fused to the candidate proteins, a positive control clone would thus be MBP fused to the biotinylation peptide. A negative control might be, for example, a clone containing a frameshift in the peptide-encoding sequence such that the peptide is either not expressed or is expressed but not fused to a soluble protein. An alternative, and optionally complementary negative control clone might encode an insoluble protein in frame with the peptide. Being insoluble, the peptide will not act as an efficient substrate for the substrate modifying protein.

Further aspects of the invention relate to kits for use in accordance with the methodology described above. For example, a suitable kit for identifying soluble variants of a candidate protein may comprise:

a) an expression vector for expression of variant candidate proteins in a host cell; wherein said vector contains restriction sites to allow insertion of a gene of interest encoding the candidate protein such that a sequence encoding a biotinylation peptide is fused genetically to the gene of interest;

b) a positive control vector that expresses maltose binding protein genetically-fused to nucleic acid encoding the biotinylation peptide;

c) a negative control vector as in b) but which includes a frameshift in the biotinylation peptide encoding sequence so the maltose binding protein is not biotinylated; and d) a further negative control vector that expresses an insoluble protein in frame with the biotinylation peptide.

The kit may also contain instructions for generating truncation libraries of genes encoding a candidate protein of interest and cloning the truncations so that they are fused to sequence encoding the peptide substrate.

Various aspects and embodiments of the present invention will now be described in more detail by way of example. It will be appreciated that modification of detail may be made without departing from the scope of the invention.

Figure 10:
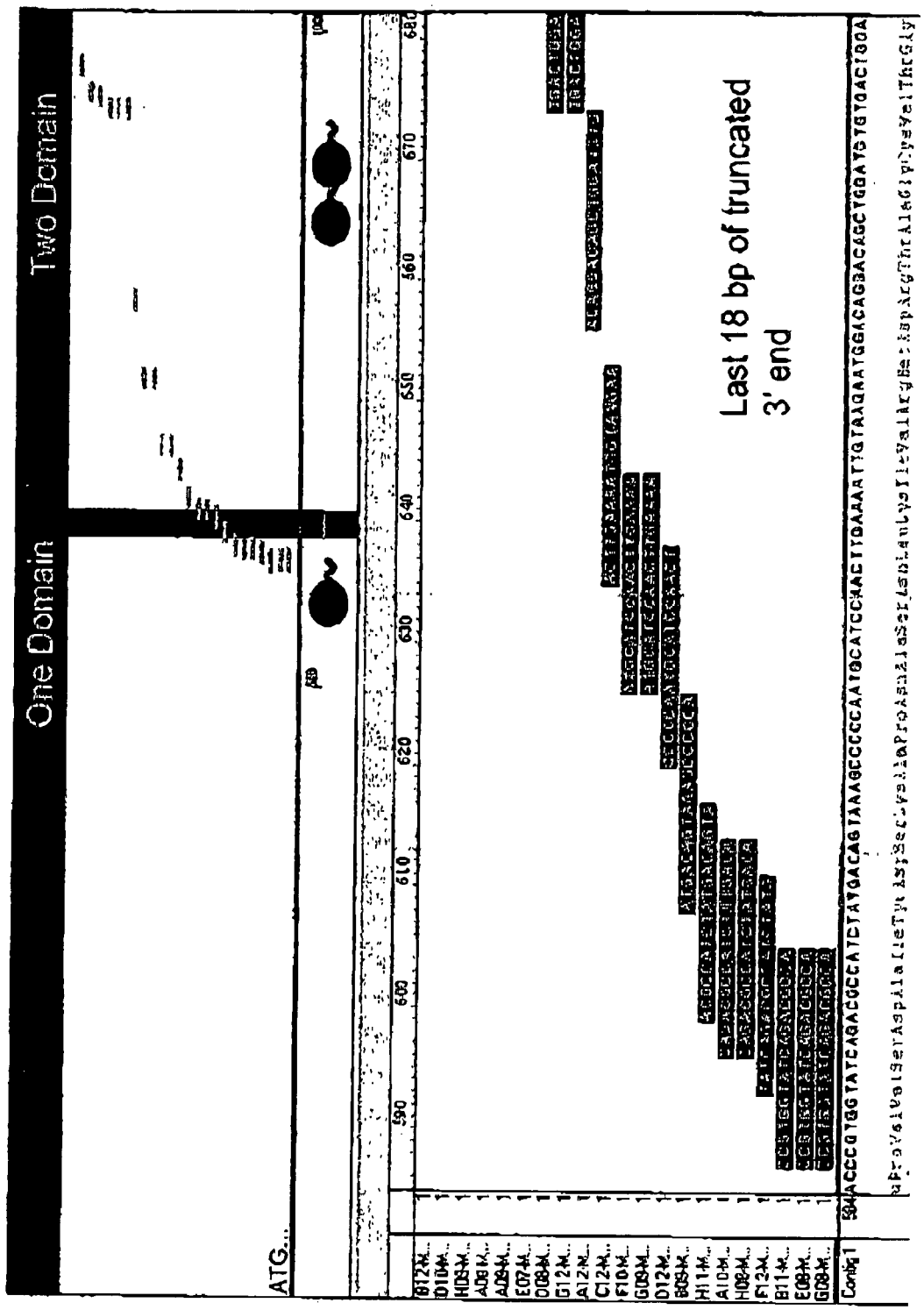
FIG. 10: Definition of exact truncation termini by alignment of the last 18 base pairs of DNA sequencing data at the truncated 3' end with the full-length gene sequence.

The sequences in FIG. 10 are identified as follows:

Row A12-M lists SEQ ID NO: 11; Row C12-M lists SEQ ID NO: 12; Row F10-M and Row G09-M list SEQ ID NO: 13; Row D13-M lists SEQ ID NO: 14; Row B09-M lists SEQ ID NO: 15; Row H11-M lists SEQ ID NO: 16; Rows A10-M and H08-M list SEQ ID NO: 17; Row F12-M lists SEQ ID NO: 18; and Rows B11-M, E08-M and G08-M list SEQ ID NO: 19. The nucleotide sequence along the x-axis lists SEQ ID NO: 20. The polypeptide sequence immediately below SEQ ID NO: 20 lists SEQ ID NO: 21.

Figure 11:
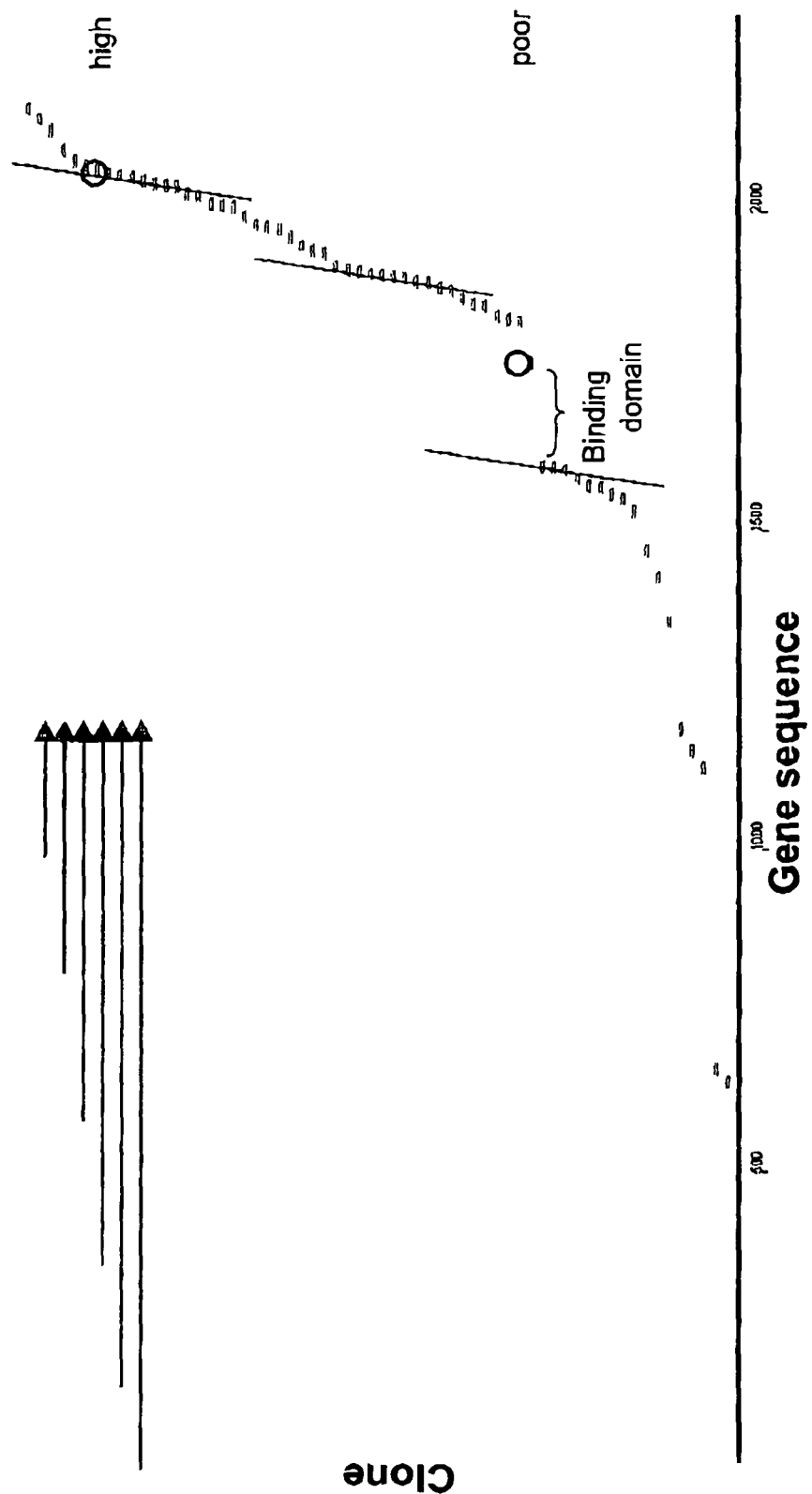

FIG. 11: Soluble expression map of the gene encoding a previously unexpressed protein correlating solubility with genetic truncation point. The positions of new start codons generated during construction of a N-terminal truncation library are aligned against the full-length gene sequence. Of the 2400 positions, 61 are indicative of soluble protein expression. The figure demonstrates a binary output (expression above a threshold limit vs non-expression) however some clones express much better than others (examples of low and high expressing clones are indicated).

Figure 12:
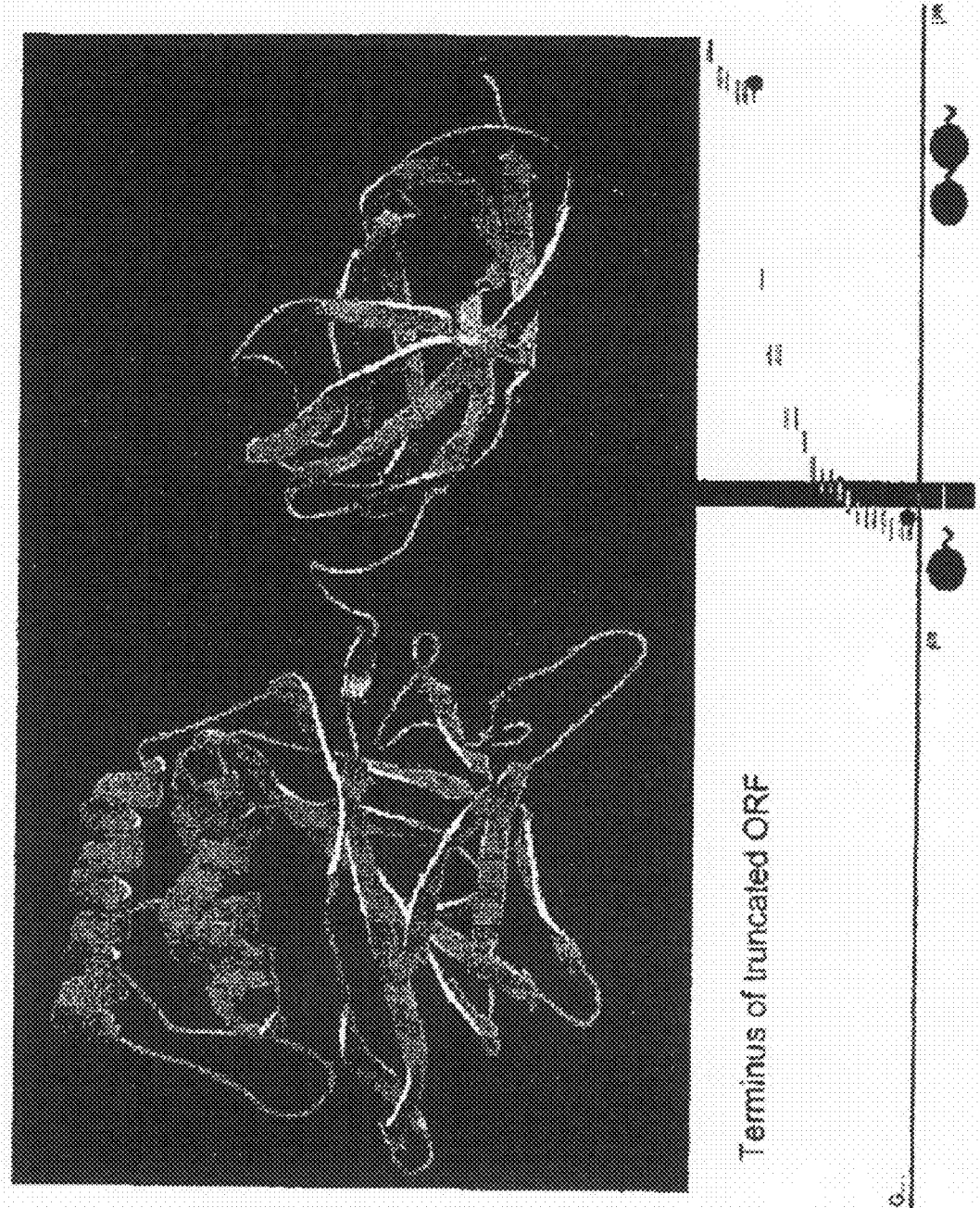

FIG. 12: Alignment of solubly expressing NF-?B constructs identified by random screening with the predetermined, full-length protein structure. High-resolution definition of domain boundaries is apparent from the clones marked with a dot. These are the most compact forms of the 1- and 2-domain constructs.

Figure 13:
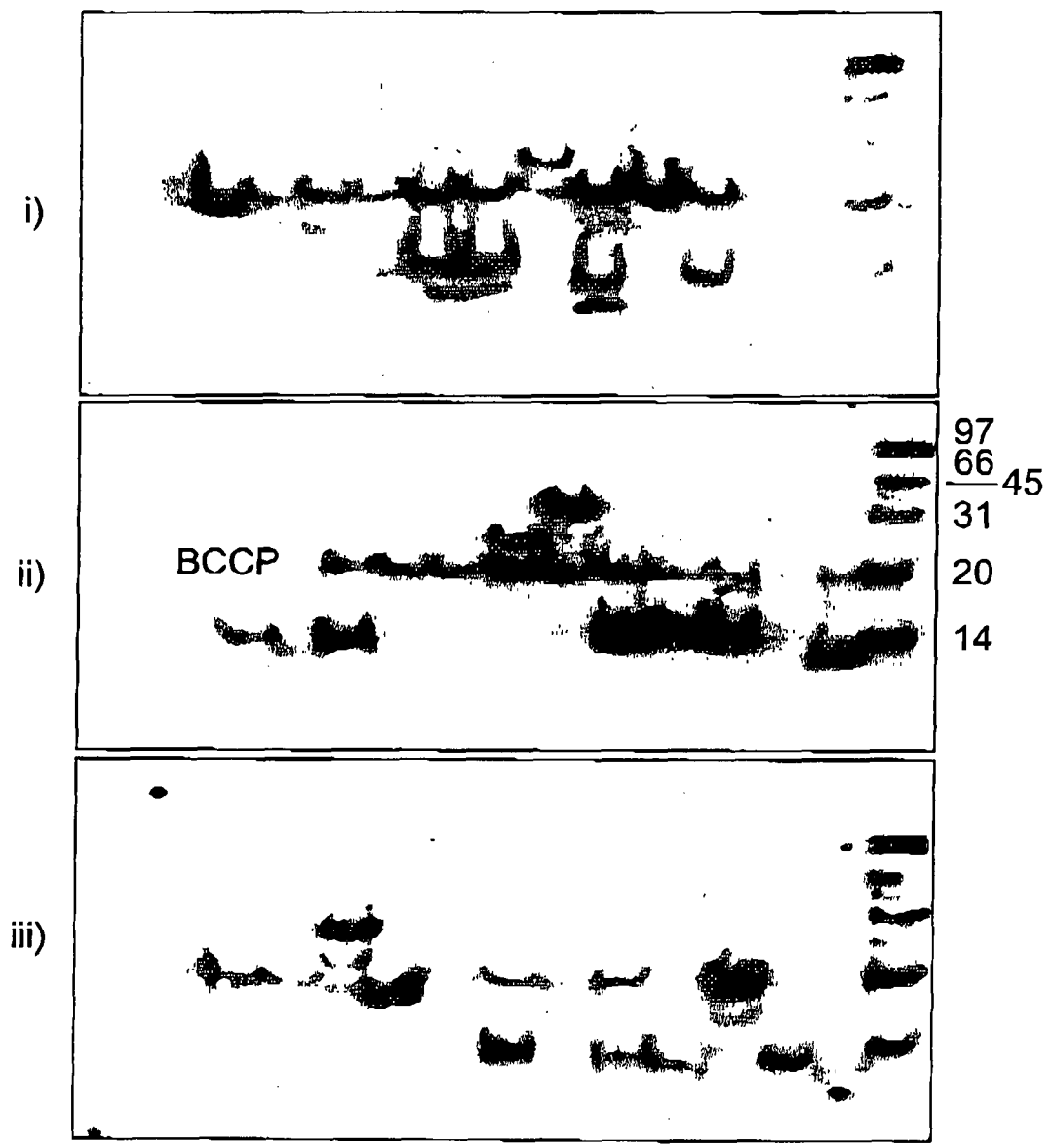

FIG. 13: Protein expression as identified using Western blot analysis. 96 positive clones from the truncation library of the gene in plasmid pHAR1111 were grown in LB. Cells were lysed, fractionated and soluble fractions were analysed by Western blot with Str-HRP. Some representative clones are shown. Recombinant proteins from Western analyses cluster according to 3 size ranges (approx 10, 20, 30 kDa) as apparent from the soluble expression map in FIG. 11. The endogenous host protein BCCP is also indicated.

Figure 1:
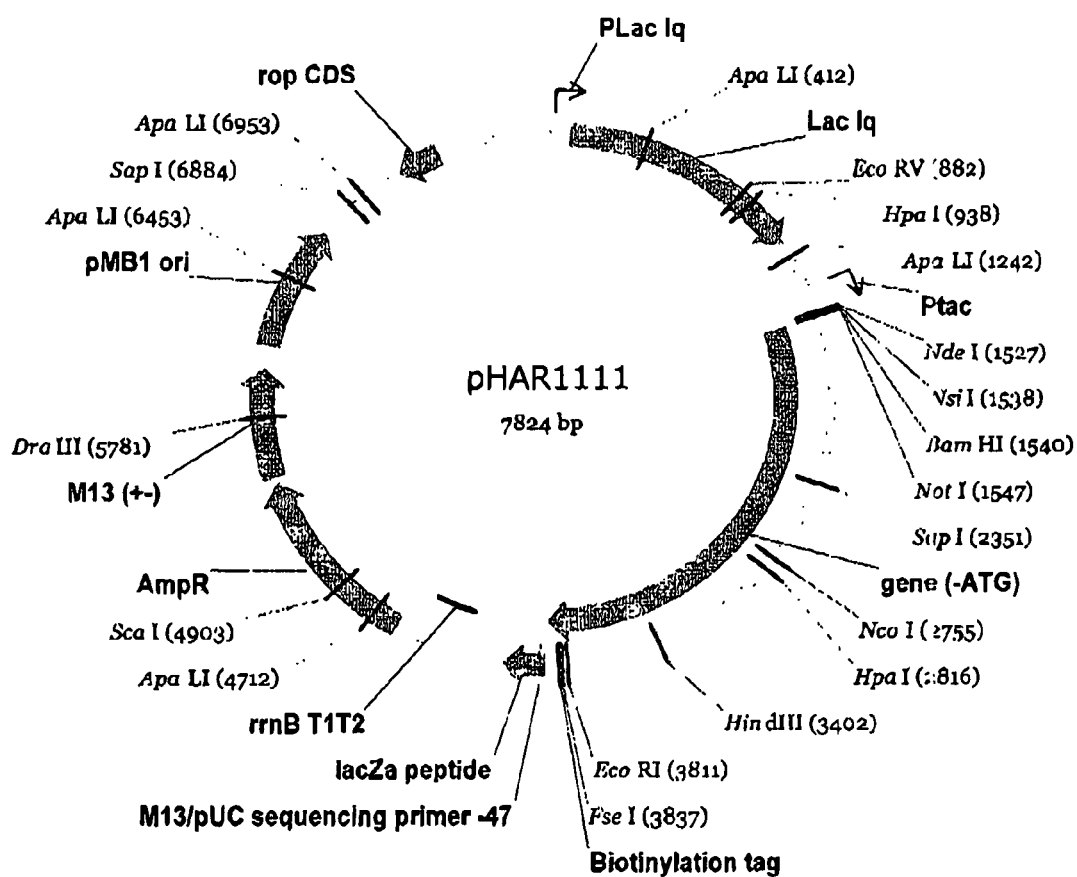
FIG. 1: Plasmid pHAR1111 encoding a candidate gene fused in frame at the 3' end to DNA encoding a biotinylation peptide and with restriction sites at the 5' end of the gene designed to permit fabrication of a N-terminal truncation series of the protein.
Figure 14:
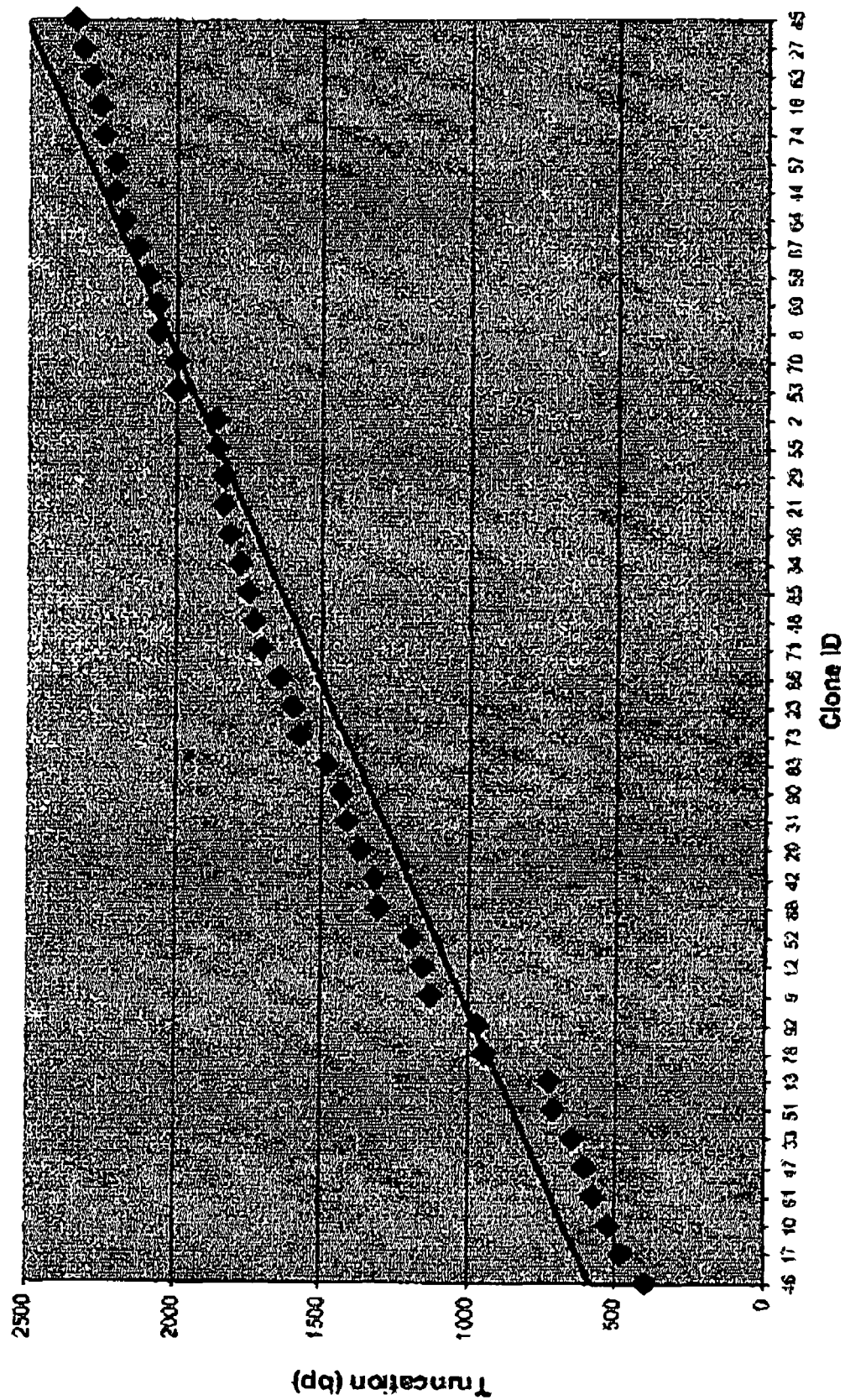

FIG. 14: Size distribution of the gene inserts from plasmid pHAR1111 (see FIG. 1) as revealed by plasmid digest. It is apparent that the exonuclease truncation protocol as performed here generates a linear and relatively unbiased distribution of gene fragment sizes permitting screening of random truncations of the target gene of all size.

Figure 15:
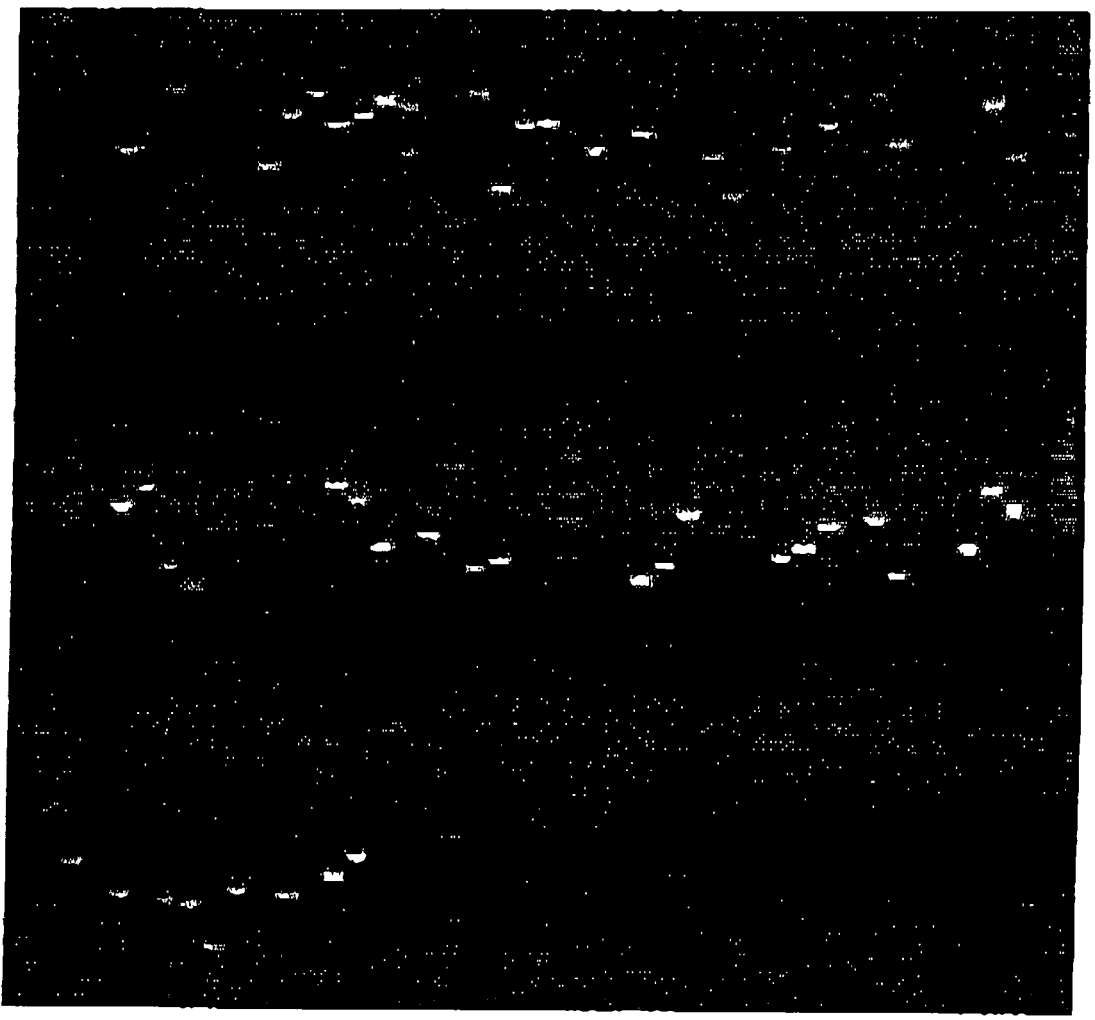

FIG. 15: Results of PCR analysis of the randomly truncated gene from plasmid pHAR1111 showing size distribution of a sample of clones in the library before solubility screening.

Figure 16:
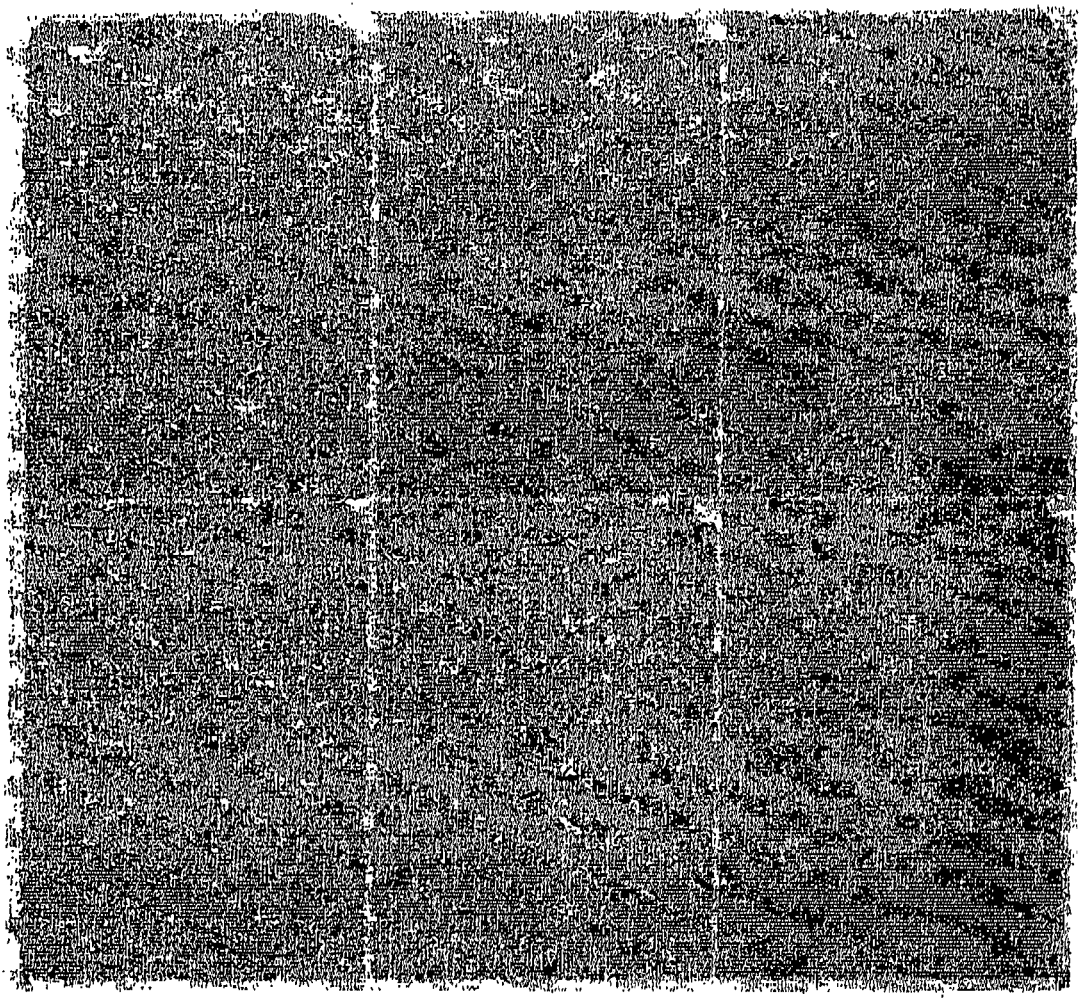

FIG. 16: Solubility screen of proteins expressed by the random truncation library clones of the gene in plasmid pHAR1111. Here the array was probed with Alexa488 fluorophor conjugated streptavidin and the image captured via a Typhoon fluorescence scanner (Amersham). Clones expressing soluble proteins are visible in a duplicate pattern for each.

Figure 17:
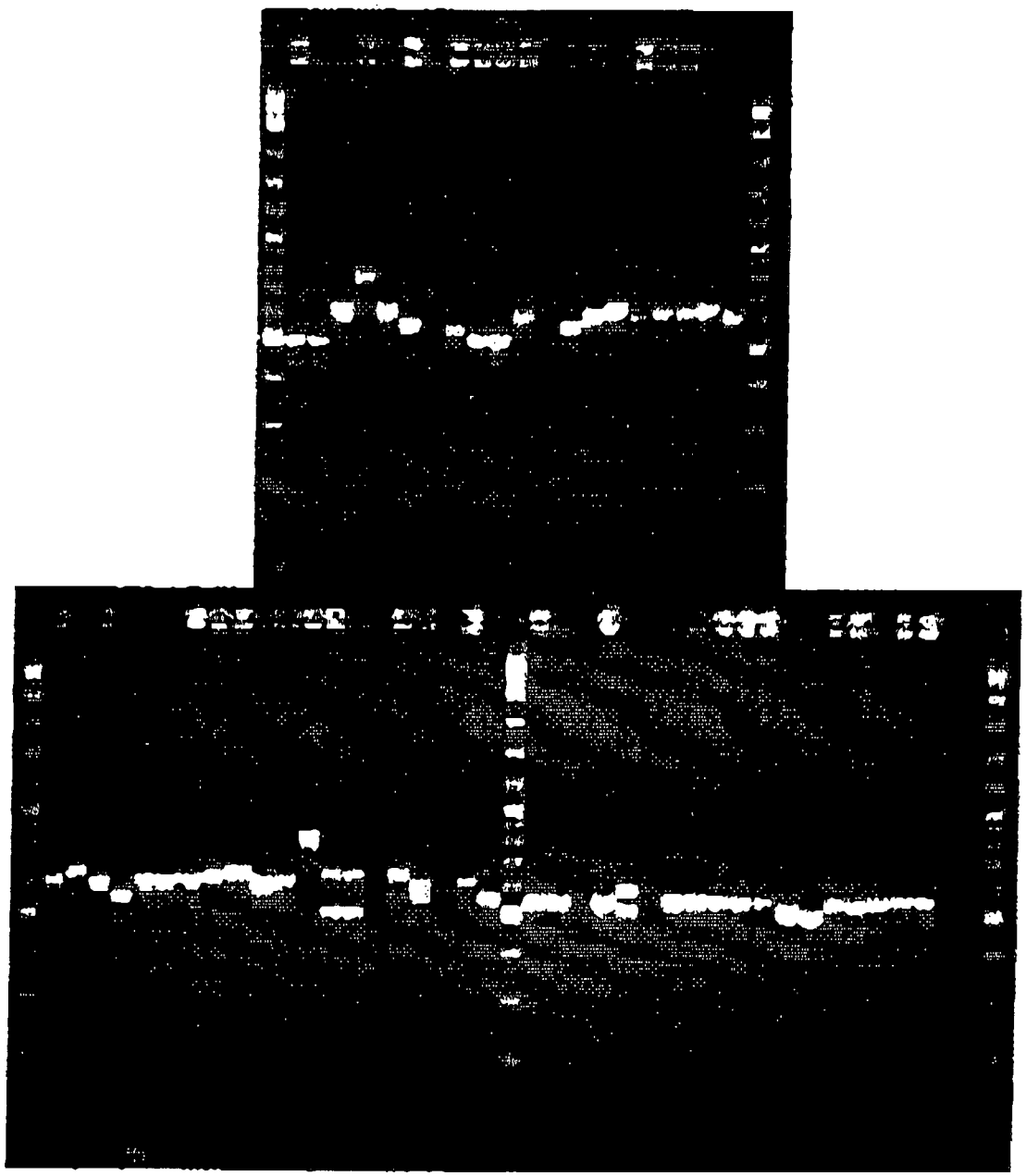

FIG. 17: Results of PCR analysis of the randomly truncated gene from plasmid pHAR1111 showing the non-random size distribution of truncations expressing soluble protein.

Figure 18:
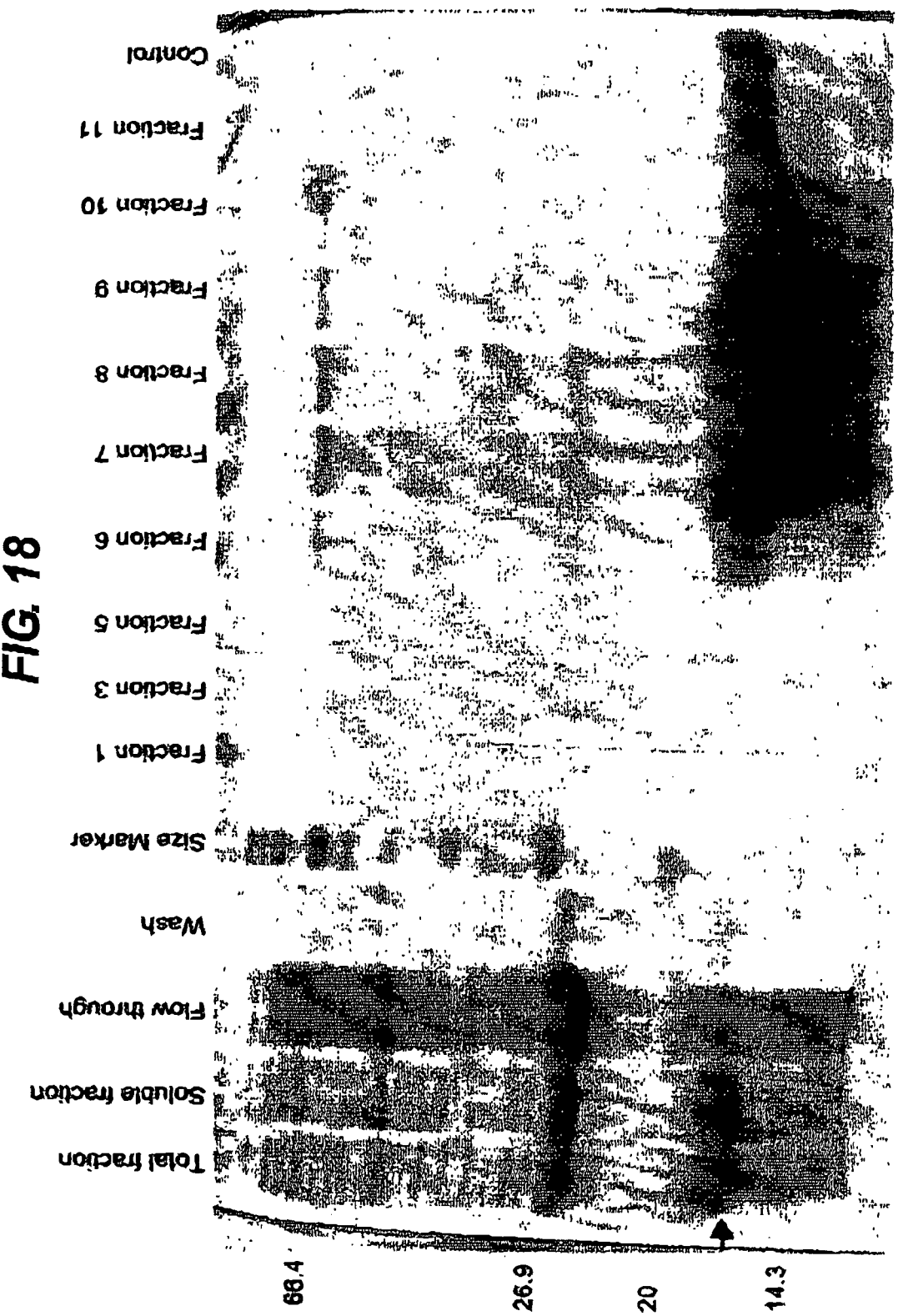

FIG. 18: Purification profile of a soluble protein fragment identified using the solubility screen. The gene fragment was first subcloned into an E. coli expression vector to add a N-terminal hexahistidine tag to facilitate purification (FIG. 19).

Figure 19:
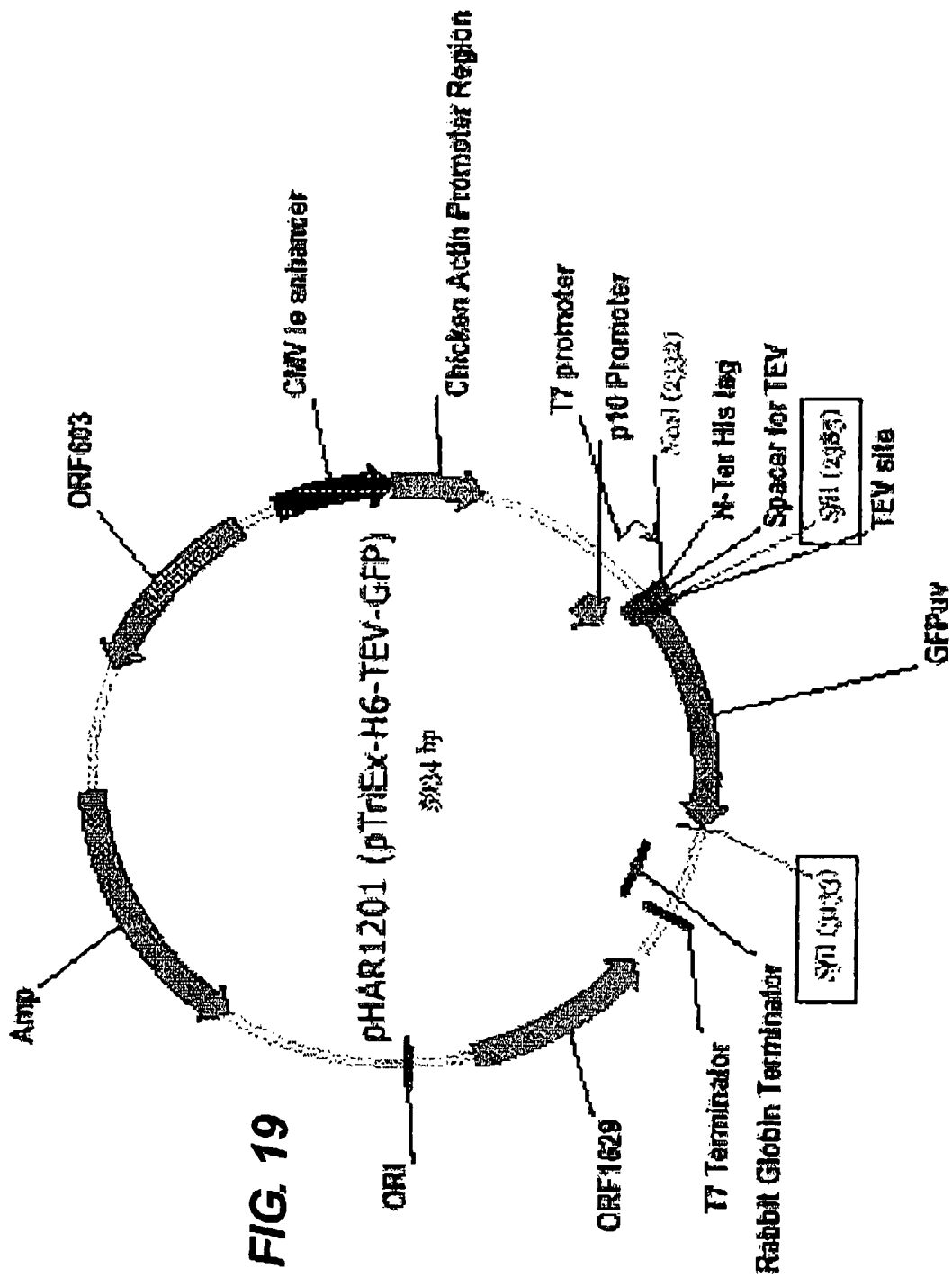

FIG. 19: A derivative of the pTriEX vector (Novagen) that was used to subclone gene fragments for scale-up of protein expression. A TEV protease cleavable hexahistidine tag is added to the N-terminal end of the construct to permit affinity purification.

Figure 20:

FIG. 20: A multidomain 30 kDa fragment of the protein expressed from pHAR1111 is obtained after fusion of the truncated gene to maltose binding protein to aid expression and purification.

Figure 21:
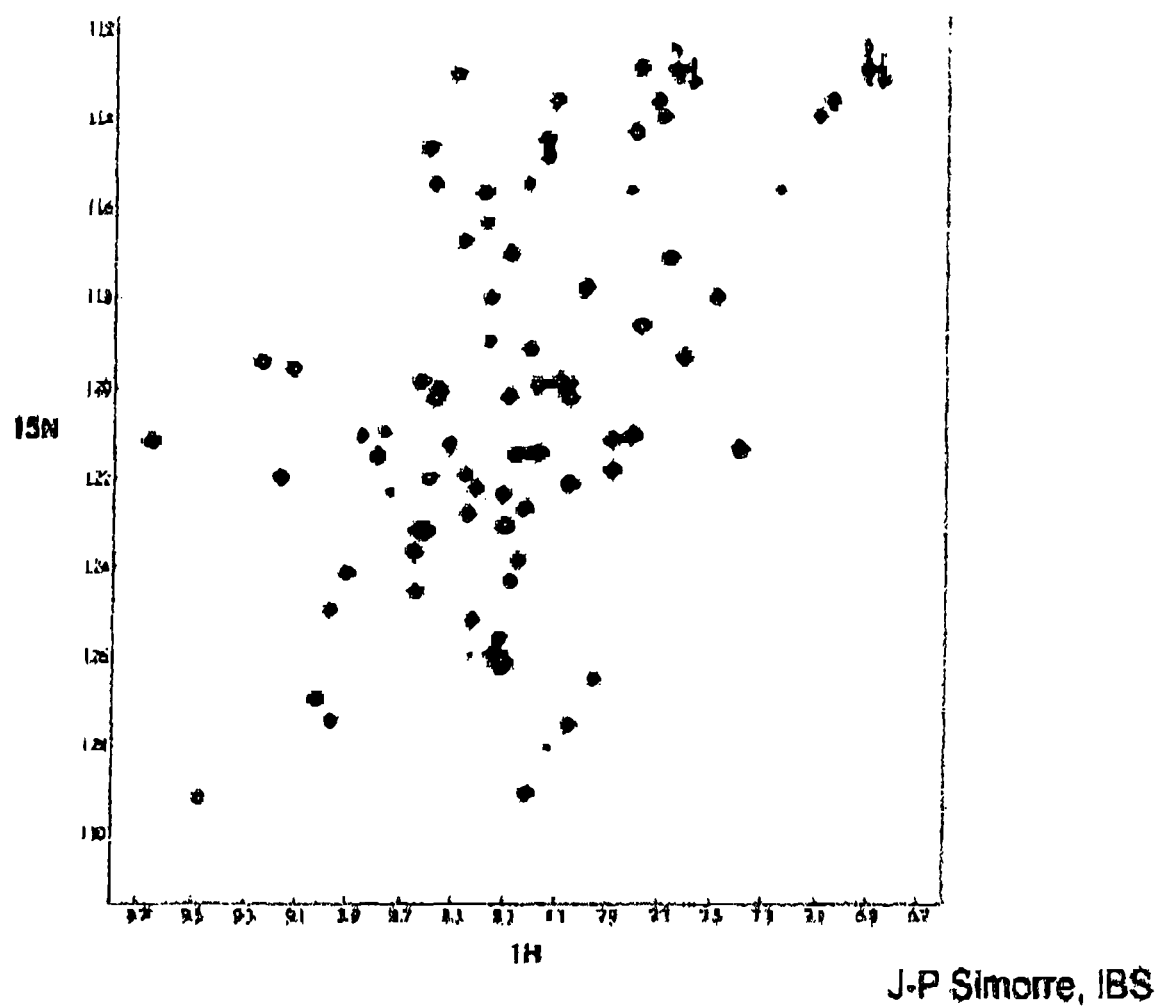

FIG. 21: Results of an HSQC NMR spectrum analysis of $^{15}$N labelled protein which confirm that the purified domain identified from the screening of the random library is well-folded in addition to being highly soluble.

Figure 22:
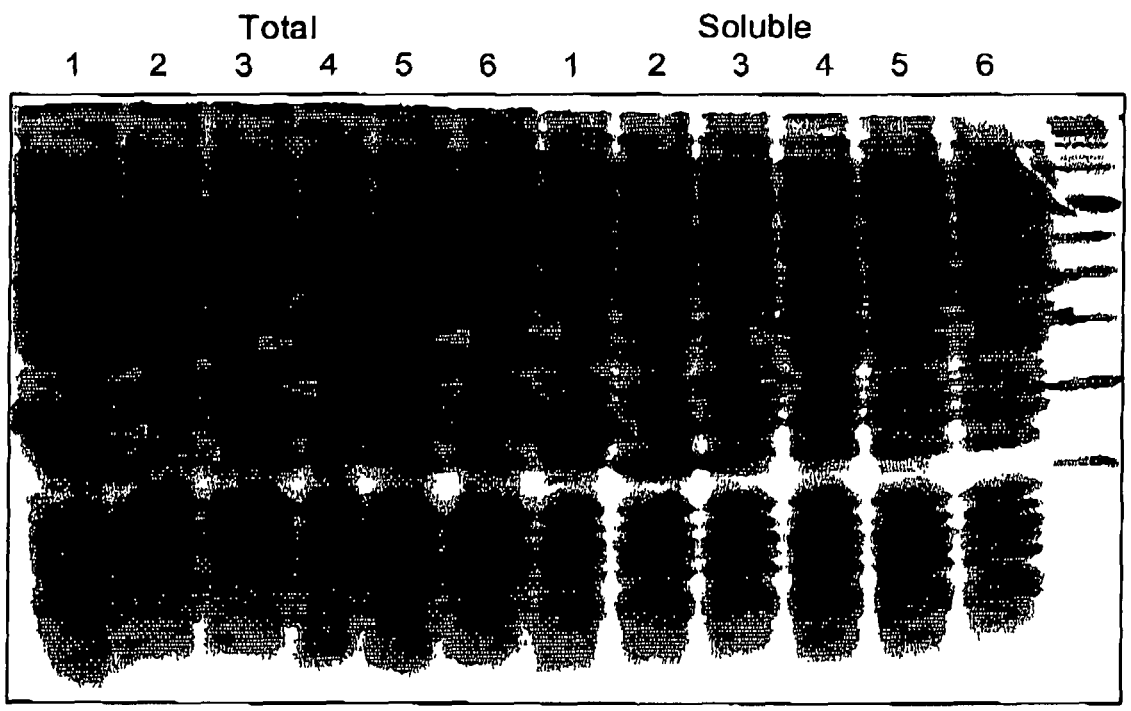

FIG. 22: An SDS PAGE gel showing the Total and Soluble fraction of protein obtained from six different colonies expressing variants of the pTAR007 target gene library.

Figure 23:
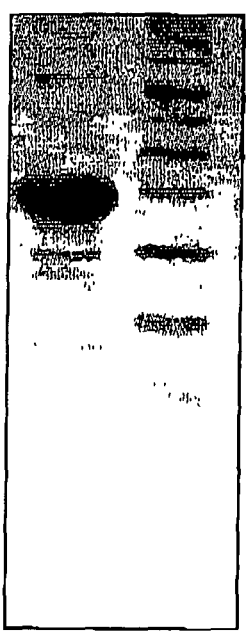

FIG. 23: An SDS PAGE gel showing a sample of affinity purified target protein.

Figure 24:
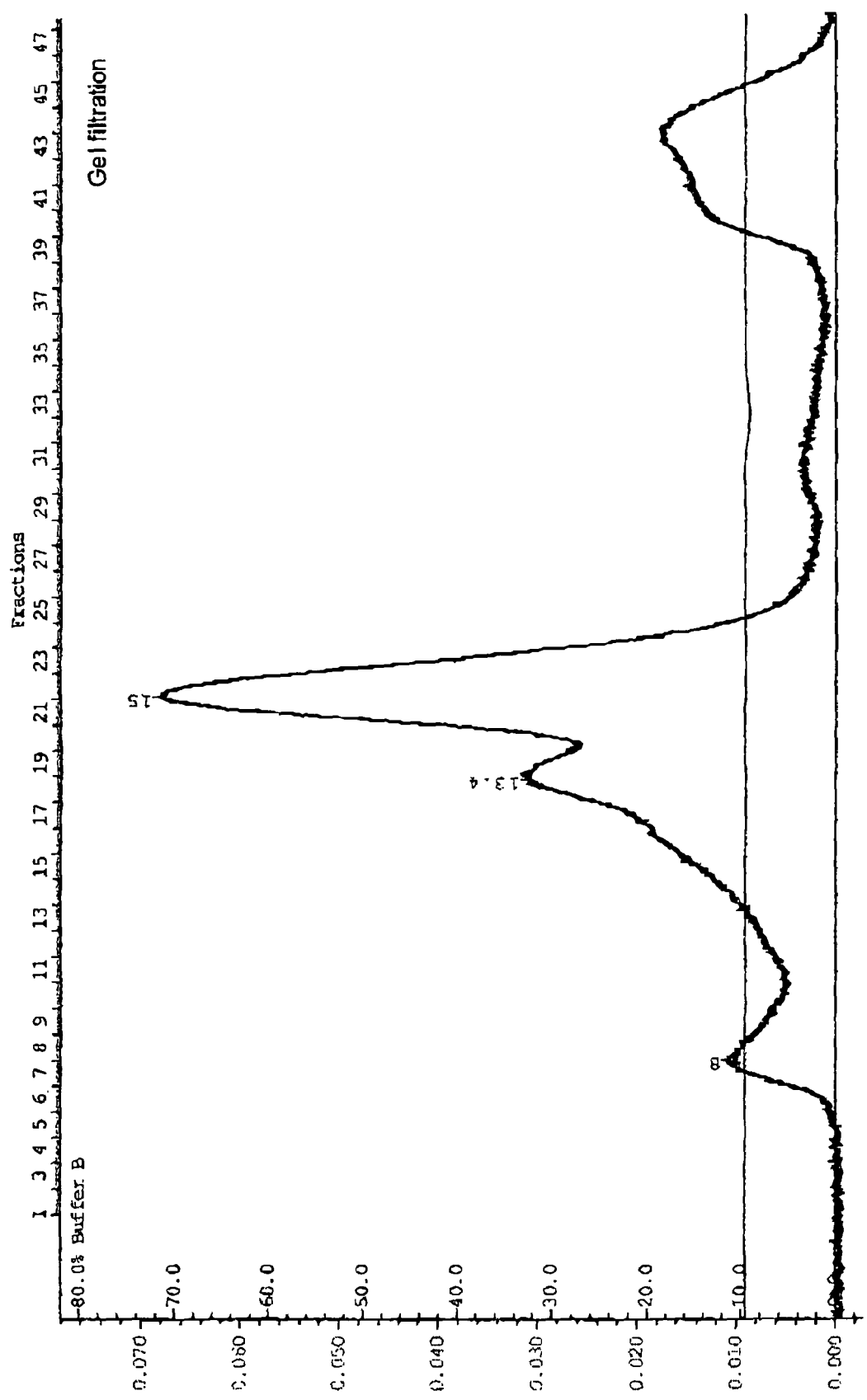

FIG. 24: Gel filtration of the target protein.

Figure 25:
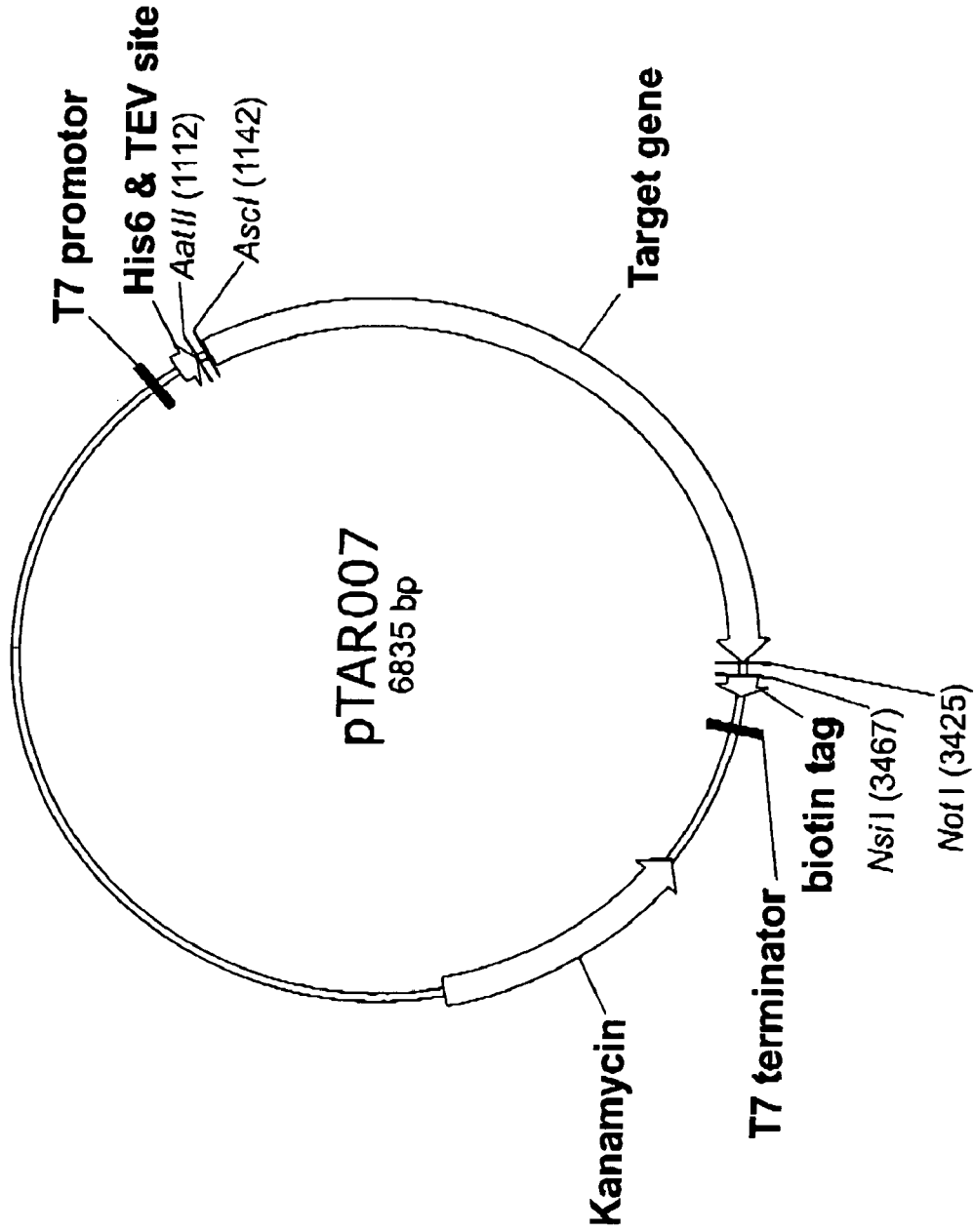

FIG. 25: Plasmid pTAR007 encoding the target gene fused in frame at the 3' end to DNA encoding a biotinylation peptide and with restriction sites at the 5' and 3' end of the gene designed to permit fabrication of an N-terminal and C-terminal truncation series of the protein.

Figure 26:
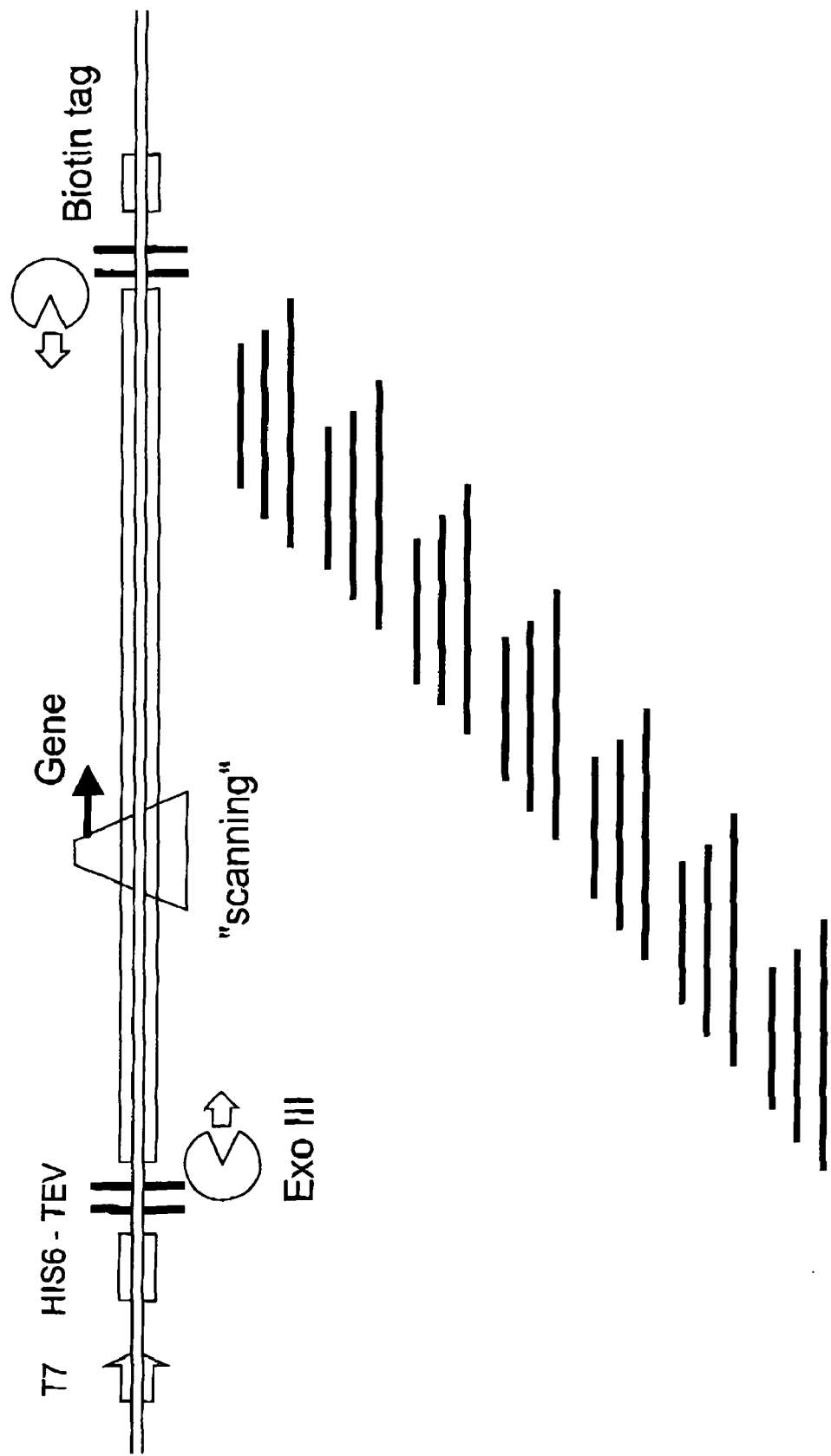

FIG. 26: Graphical representation of the bidirectional truncation method showing the gene of interest flanked by two unidirectional cut sites.

Figure 27:
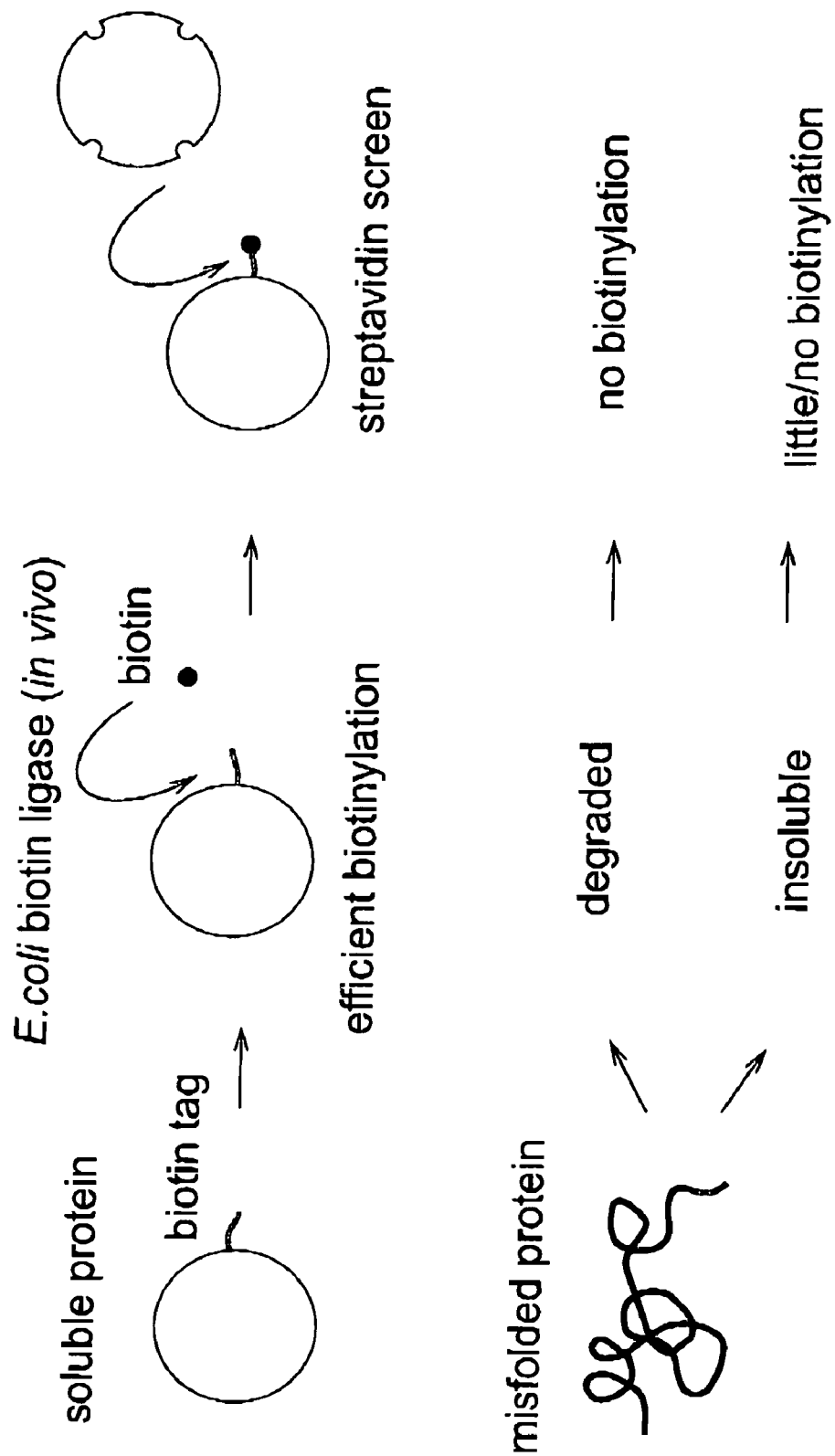

FIG. 27: Schematic representation of the methodology of the present invention. If the protein produced is soluble then the biotin tag is also soluble and is readily biotinylated and detected via streptavidin screening. If the protein produced is insoluble or degraded, then biotinylation is inefficient and easily distinguishable from soluble clones.

RESULTS & METHODS

Examples—Proof of Concept of Methodology Applied to a 1) a Candidate Gene encoding a previously unexpressed protein and 2) the Human NF-kappa B gene encoding a protein of known structure for validation purposes Construction of Vectors Allowing Analysis of N-Terminal Truncations of Proteins Encoded by the Inserted Gene of Interested.

A plasmid for general usage in solubility screening was initially constructed by assembling a vector containing a gene of interest together with relevant features enabling the truncation process. This initial construct was used in the analysis of the candidate gene, but also as the source of plasmid for cloning any other gene of interest by direct, simple replacement of the candidate reading frame for another. The construction of the candidate gene-containing construct is described followed by that of a derivative construct containing a different, unrelated gene, NF-kappaB.

a) PCR of the Candidate Gene

The candidate gene was cloned by PCR from a previous plasmid containing the open reading frame. PCR reactions were performed in 50 ul reactions using PWO polymerase (Roche) according to the instructions provided. The PCR construction used 4 oligonucleotides primers in a strategy whereby small outside primers amplified the initial amplicon produced by priming of the large oligos (to increase efficiency of the reaction): 60 nM for 1
[5'GATCCTAGCATATGAAATGCATGGATC-CGCGGCCGCTGAXXXXXXXXXXXXXXX XXXXX-3'] (SEQ ID NO: 3) where X indicates a complementary base to the candidate gene sequence omitting the ATG start codon, 600 nM for 2 [5'-GATCCTAGCATATGAAATGCATGG-3'] (SEQ ID NO: 4), 60 nM Fse1rev1 [5'-GATCCTAGGGCCG-GCCXXXXXXXXXXXXXX-3'] (SEQ ID NO: 5) and 600 nM Fse1rev2 [5'-GATCCTAGGGCCGGCCXXXXX-3'] (SEQ ID NO: 6) PCR conditions were 94° C., 2 min and then 25 cycles of 94° C., 30 sec; 45° C., 30 sec; 72° C.; 2 min.

The PCR was electrophoresed on 1% TBE agarose, the bands excised and DNA products purified using a QIAEXII kit (Qiagen) To generate insert for cloning, 1 ug of the PCR product was digested to completion with NdeI and FseI and the 2230 bp DNA fragment then gel purified by QIAEXII.

b) Construction of a Vector Containing DNA Encoding the Biotinylation Peptide and Suitable Restriction Sites for Cloning the Candidate PCR Product An oligonucleotides cassette was generated by annealing two oligos biot-1_for [5'-AGCTTGCTTGGTGGCGGTCT-GAACGACATCTTCGAGGCTCAGAAAATCGAATGGC ACGAATAATGAG-3'] (SEQ ID NO: 7) and biot-1_rev [5'-AGCTCTCATTATTCGTGCCATTC-GATTTTCTGAGCCTCGAAGATGTCGTTCAGACC GCCACCAAGCA-3'] (SEQ ID NO: 8). This was ligated into the HindIII site of pMAL-c2g [New England Biolabs] forming the intermediate plasmid pMAS103 which was then digested with NdeI and FseI. The 5521 base pair fragment (the vector backbone) was gel purified as above and dephosphorylated with Shrimp Alkaline Phosphatase (Amersham).

c) Cloning of the PCR Product into an *E. coli* Expression Vector

The 2230 base pair candidate gene insert was then ligated to the 5521 base pair pMAS103-derived backbone with T4 DNA ligase (Rapid Ligation Kit, Roche) and the reaction was subsequently desalted using a PCR Quick column and eluted in 35 ul of 10 mM Tris Cl pH 8.0. The *E. coli* strain DH5alpha was transformed by electroporation with the 2 ul of desalted ligation reaction, recovered for 1 hour in SOC medium and plated on LB agar supplemented with ampicillin to 70 ug/ml. Plasmids were isolated from several colonies and were characterised by restriction digest and DNA sequencing to confirm the correctness of the construction: pHAR1111 (see FIG. 1).

Plasmid pHAR1111 was used in a gene truncation experiment for the candidate gene. It was also used as a starting vector for analysis of other genes: the candidate gene was excised by plasmid digestion with NotI and FseI and alternative genes inserted by ligating genes with compatible NotI and FseI sites, introduced by PCR, at equivalent positions relative to the start and stop codons of the open reading frame.

Figure 2:
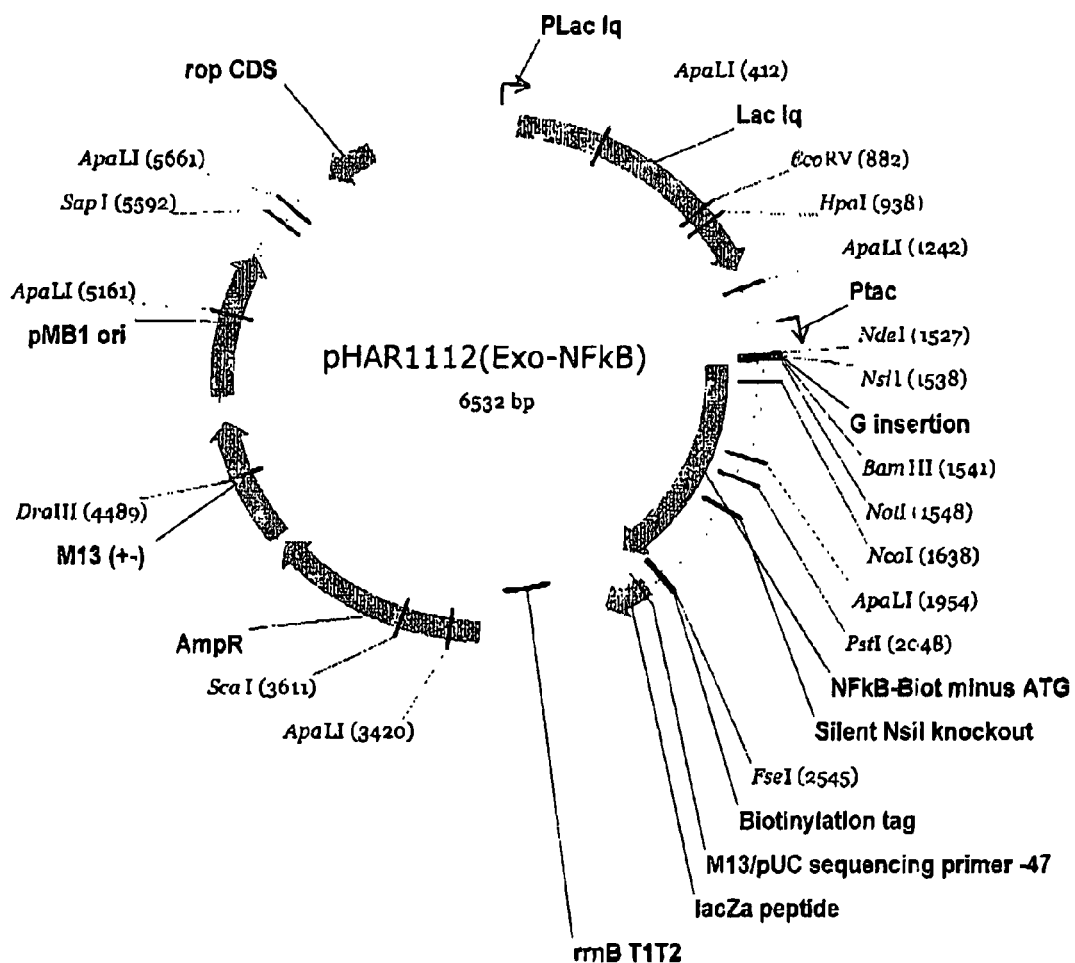
FIG. 2: Plasmid pHAR1112 encoding the human NF-kappa B gene fused in frame at the 3' end to DNA encoding a biotinylation peptide and with restriction sites at the 5' end of the gene designed to permit fabrication of a N-terminal truncation series of the protein.

For example, the human NF-kappaB gene was initially mutated to silently remove an internal NsiI site. It was then amplified by PCR with oligonucleotides primers NFkBfor1 [5'-GGATCCGCGGCCGCTGAGCAGATGGC-CCATACCTTCAAATATTAGAGC-3'] (SEQ ID NO: 9) and NfkBFseRev1 [5'-GGGATCCGGCCGGCCCCTTCT-GACGTTTCCTCTGCACTTCTTC-3'] (SEQ ID NO: 10) resulting in a gene in which the original start codon had been removed. The PCR product was digested with NotI and FseI and ligated in to vector backbone derived by NotI and FseI digest of pHAR1111. Thus the NF-kappaB gene was generated in a form compatible with N-terminal deletion of the protein encoded by the gene (vector pHAR1112; FIG. 2).

In summary, two similar vectors were produced permitting 5' deletion libraries to be made: pHAR1111 contained a previously unexpressed candidate gene; pHAR1112 contained the gene for the transcription factor NF-kappa B, a protein of known structure that could be used for validation purposes.

d) Construction of Vectors Allowing Analysis of C-Terminal Truncations Of Proteins Encoded by the Inserted Gene of Interest.

The vector pMAS103 (described above) formed the basis of a second construct enabling digestion at the 3' end of the gene of interest. Here candidate genes were cloned full-length as DNA fragments in which the start codon (ATG) is present in an NdeI site (CATATG) and where the stop codon is followed by any form of end compatible with the BamHI, XbaI, SalI or HindIII sites of the pMAS103 vector (either as compatible overhang or by blunt-end ligation).

To exemplify this, the Human NF-kappaB gene was excised by NdeI and BamHI digest from another plasmid (pHAR307) that contained the gene fused to DNA encoding a C-terminal hexahistidine tag (the tag has no significance in this experiment). This fragment was ligated to pMAS103 vector backbone prepared by digestion with NdeI and BamHI.

Figure 3:
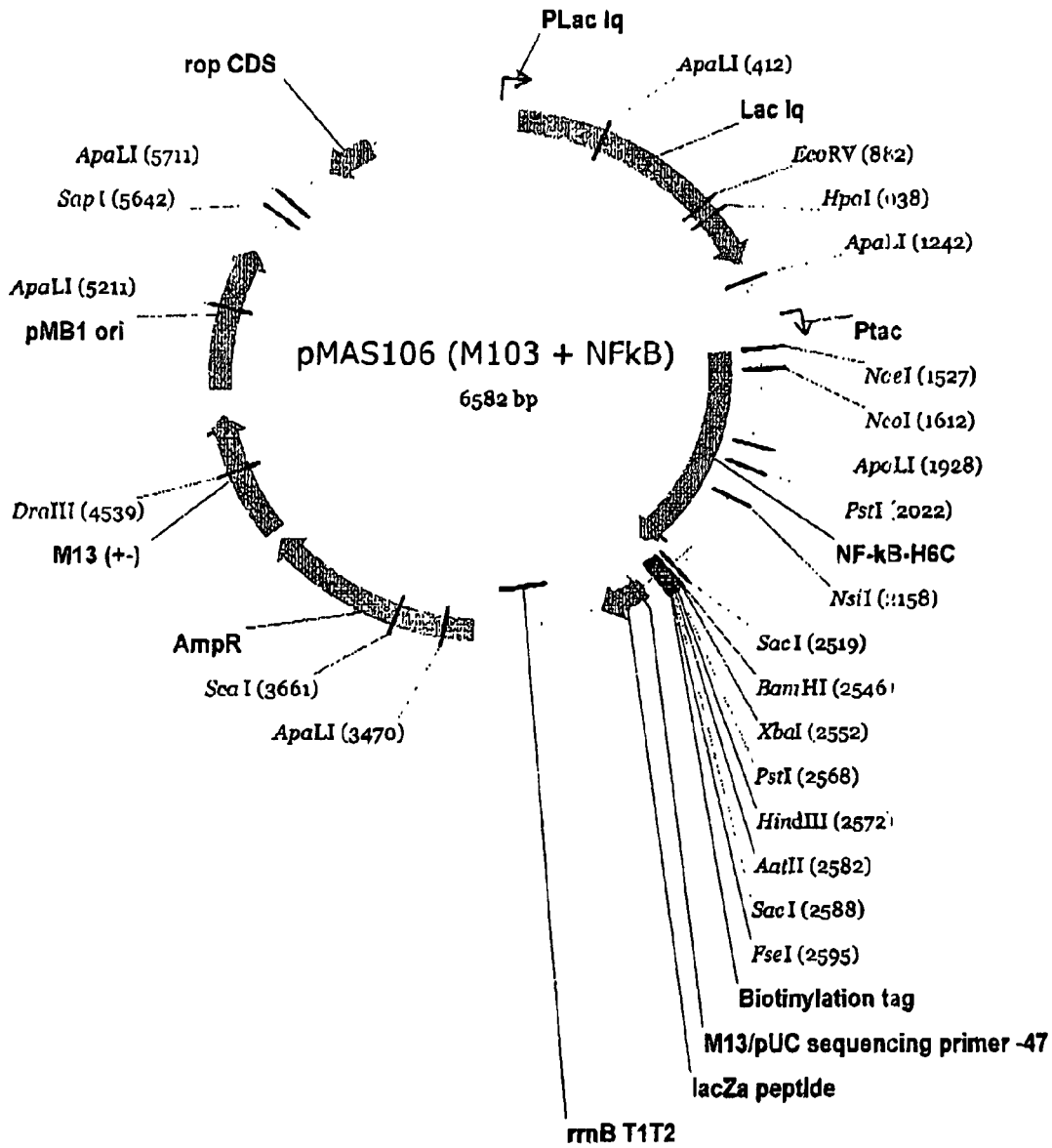
FIG. 3: Plasmid pMAS106 encoding the human NF-kappa B gene in frame at the 5' end adjacent, but not in frame with DNA encoding a biotinylation peptide at the 3' end and with restriction sites at the 3' end of the gene designed to permit fabrication of a C-terminal truncation series of the protein.

In summary, the plasmid, pMAS106 (FIG. 3) contains the NF-kappaB insert in a form compatible with C-terminal deletion of the protein encoded by this gene. This was subsequently used for validation purposes since the protein structure of NF-kappa B is well-characterised.

Truncation Protocol (Described for the Vector pHAR1111 Containing a Gene for a Previously Unexpressed Protein)

The truncation protocol was performed according to the ITCHY method (see The Creation ITCHY Hybrid Protein Libraries in Methods in Molecular Biology by Ostermeier, M. & Lutz, S., vol 231, pp 129-141). Briefly, in order to enzymatically truncate the gene of interest, 10 micrograms of plasmid pHAR1111 was digested to completion with NotI and NsiI. 4 micrograms of purified, linearised vector was diluted in 1× buffer 1 (New England Biolabs), 80 mM NaCl (in addition to that in the buffer) and in a final volume of 120 microliters. Immediately, 30 microliters was removed in to 150 microliters of PB buffer (Qiagen) forming a t=0 sec control. To the remaining 90 microliters at 22° C., 150 units of Exonuclease III was added and mixed. At 30 second intervals, 0.5 ml microliters of the enzyme-DNA reaction was removed and added to a single "quenching tube" comprising 300 microliters of PB buffer on ice. This was continued for a total of 1 h until 90 microliters of the reaction mix had been transferred. The remaining 30 microliters formed the t=1 h control and was also added to 150 microliters of PB buffer. The three reactions (t=0, t=1 h and the library) were cleaned up using PCR cleanup spin columns (Qiagen) and eluted in 30 microliters, 30 microliters and 50 microliters of EB buffer respectively). The control samples were analysed on gel to verify the exonuclease reaction (data not shown)

In order to remove the single stranded overhang left after the exonuclease digest, the 50 microliters of library mix was diluted in 1× Mung Bean Nuclease (MBN) buffer (New England Biolabs) and 3 units of MBN enzyme added in a final volume of approximately 55 microliters. The reaction was then incubated at 37° C. for 30 mins. The reaction was cleaned up using PCR cleanup spin columns and eluted in 65 microliters of EB.

To polish the ends of the vector prior to ligation, 48 microliters of the library DNA was diluted in 1×T4 DNA polymerase buffer (New England Biolabs) with 2.5 mM dNTPs and 1 unit of T4 DNA polymerase in a final volume of 100 microliters. The reaction was incubated at 12° C. for 20 min and then quenched by addition of EDTA to 10 mM final concentration and heating to 75° C. for 20 min.

The reaction mix was loaded onto a 0.5% TBE agarose gel and electrophoresed to separate DNA fragments by size. DNA in the size range of interest (>5.5 kilobases) was excised from the gel, purified using QIAEXII resin (Qiagen) and eluted in 60 microliters of EB.

The size-selected DNA corresponding to linearised vector containing truncated gene fragments was the recircularised by ligation with T4 DNA ligase by incubating 8 microliters of DNA solution from the QIAEXII purification with reagents from the Roche Applied Science Ligation Kit according to the manufacturer's instructions. The ligation mix was desalted using a PCR cleanup spin column and 2 microliters was used to transform *E. coli* DH5alpha competent cells by electroporation. After recovery of the trans formation mix in SOC media, the library was plated out on 22 cm square agar plates (Genetix, UK). After overnight growth at 37° C., approximately 24,000 colonies were scraped from the agar, resuspended in PBS and plasmid prepared from a small aliquot of cells using a miniprep kit (Qiagen). This plasmid was used to transform the protein expression strain of *E. coli*, BL21 Codon Plus RIL (Stratagene). The even size distribution of truncations was confirmed by a colony PCR screen of 96 clones with flanking primers and agarose gel electrophoresis.

Robotic Handling of Library.

Colony Picking

The BL21 Codon Plus RIL transformed with the plasmid library was plated out on 22 cm square LB agar plates (ampicillin 70 mg/l; chloramphenicol 30 mg/l) at a density of approximately 4,000 colonies per plate grown at 30° C. 26,880 colonies were robotically picked, using a Kbiosystems gridder-picker robot, into 384 well plates filled with 70 to microliters LB-HBFM medium per well (supplemented with ampicillin and chloramphenicol). Liquid cultures were grown overnight to saturation at 30° C. in a HiGro shaker incubator (Genomic Solutions).

Gridding onto Membranes

Figure 4:
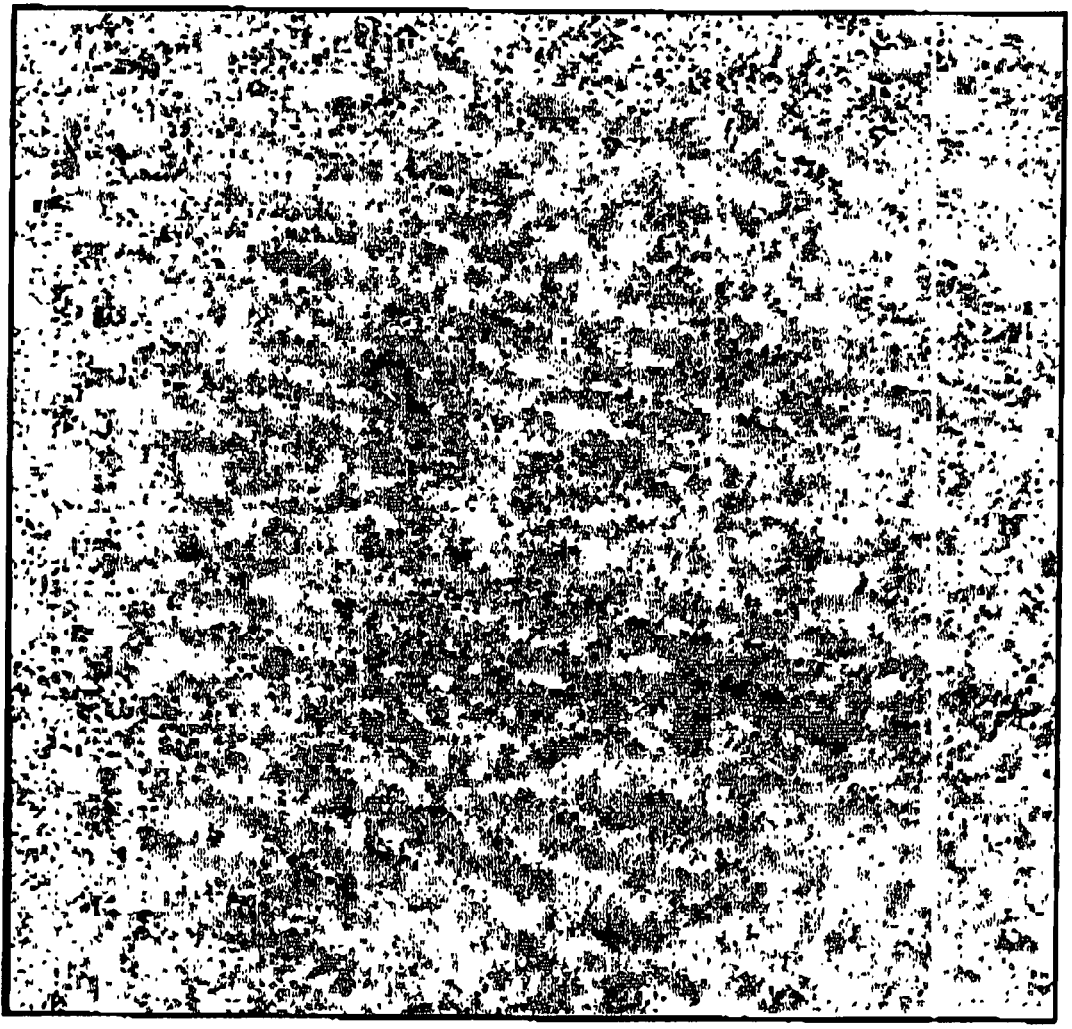
FIG. 4: Expression analysis. Picture 1a shows the full array probed with an antibody to the peptide tag after immediate lysis. Total expression (not soluble expression) is apparent.

Squares of nitrocellulose membrane (Amersham) were cut and laid on the top of 22 cm LB agar plates (supplemented with ampicillin and chloramphenicol). Using a gridding pin tool and the arraying robot, the cultures were printed on to the membranes at high density. Plates were then incubated overnight at 25° C. until colonies were just visible to the naked eye. The membranes were lifted from the agar and laid over fresh LB agar plates (supplemented with ampicillin and chloramphenicol) that were supplemented with IPTG at a final concentration of 0.1 mM to induce recombinant protein expression within the colonies. Immediate lysis and detection of the full array with antibody against the biotinylation peptide at this point leads to the detection of clones which express protein (either soluble or insoluble; FIG. 4). Membranes were incubated for 4.5 h at 30° C., lifted from the inducing agar and placed at minus 80° C. Prior to analysis, the membranes are warmed to room temperature and laid over filter paper soaked in 0.5M NaOH, 1.5M NaCl for 10 mins at room temperature. The membranes are then neutralised with 2×5 min in 1M Tris HCl, pH7.5; 1.5 M NaCl and then for 15 min in 2×SSC buffer. The membrane was then blocked overnight with Superblock (Pierce).

Hybridisation with Streptavidin and Antibody Against Peptide Tag

Detection of Expressed Proteins

A mouse monoclonal anti-avitag antibody (Avidity) was diluted 1:7,500 in 40 ml of PBS-T and added to the membrane in a Roller Blot hybridisation oven (Techne) for 2 h at room temperature. The membrane was then washed with 3 changes of PBS-T buffer for 5 min each. An antimouse peroxidase conjugate was diluted 1:25,000 in 40 ml of PBS-T and added to the membrane in a Roller Blot hybridisation oven (Techne) for 1 h at room temperature. The membrane was then washed with 3 changes of PBS-T buffer for 5 ml each. Detection of proteins was using chemiluminescent substrates for horseradish peroxidase (Amersham ECL reagent) and autoradiography (FIG. 4). Signals were quantified by densitometry.

Stripping of Membrane

Antibodies were removed by incubating the membrane in stripping buffer (PBS; 2% SDS w/v; 100 mM beta mercaptoethanol) for 30 min at room temperature. The membrane was then washed for 30 min in PBS-T and then blocked with Superblock.

Detection of Biotinylated Proteins

Figure 5A:
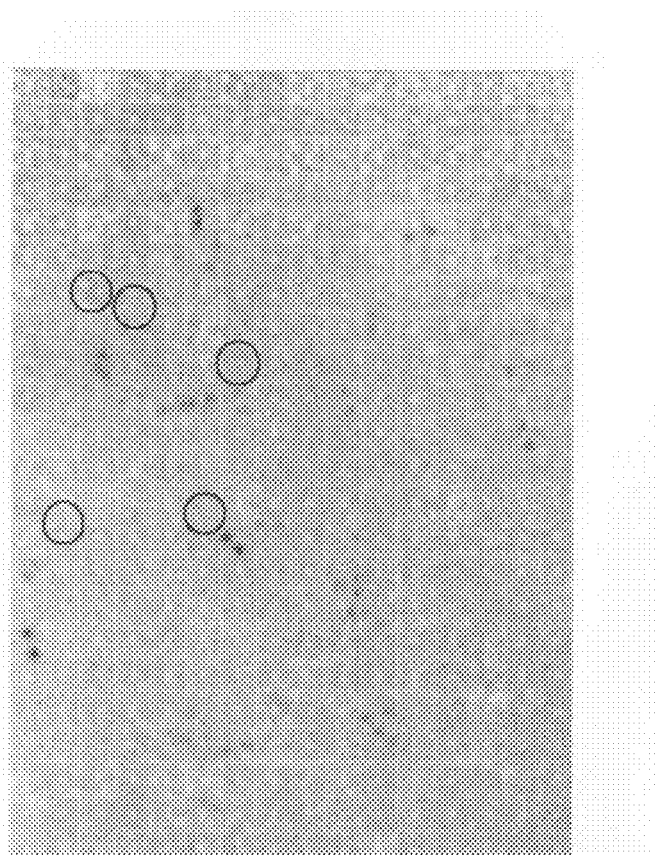
FIG. 5: Expression analysis showing identification of biotinylated proteins indicating solubility. One field out of six is shown in the FIGS. 5a and 5b and comprises a 5×5 array (24 plates per field). Proteins are identified through binding of a streptavidin-horseradish conjugate. Results were obtained from replicate arrays uninduced prior to cell lysis (FIG. 5a) and induced with IPTG (FIG. 5b). Evidence of IPTG-induced protein expression can be seen on the second membrane. Slides are analysed quantitatively (5c) using image analysis software (VisualGrid; GPC Biotech).
Figure 5B:
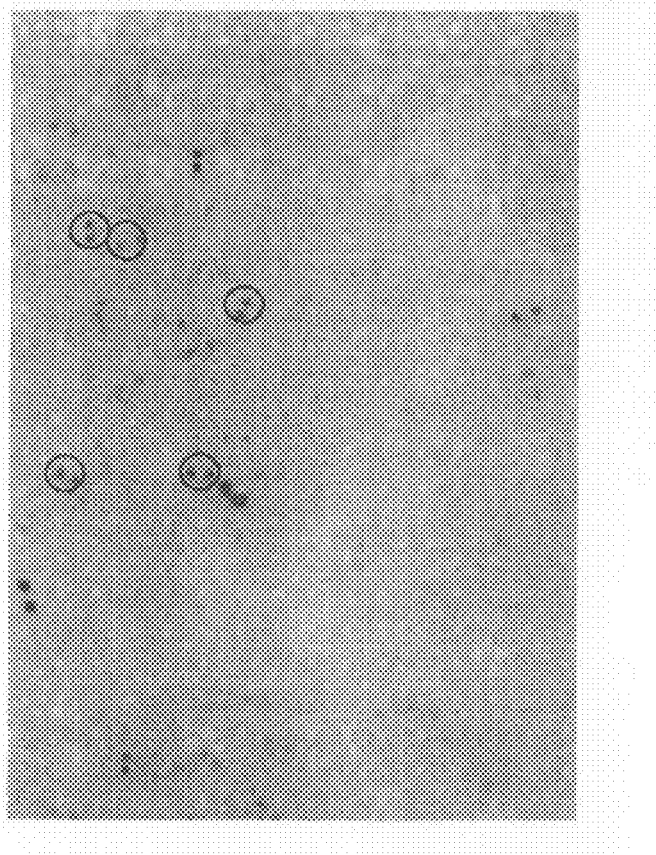
Figure 5C:
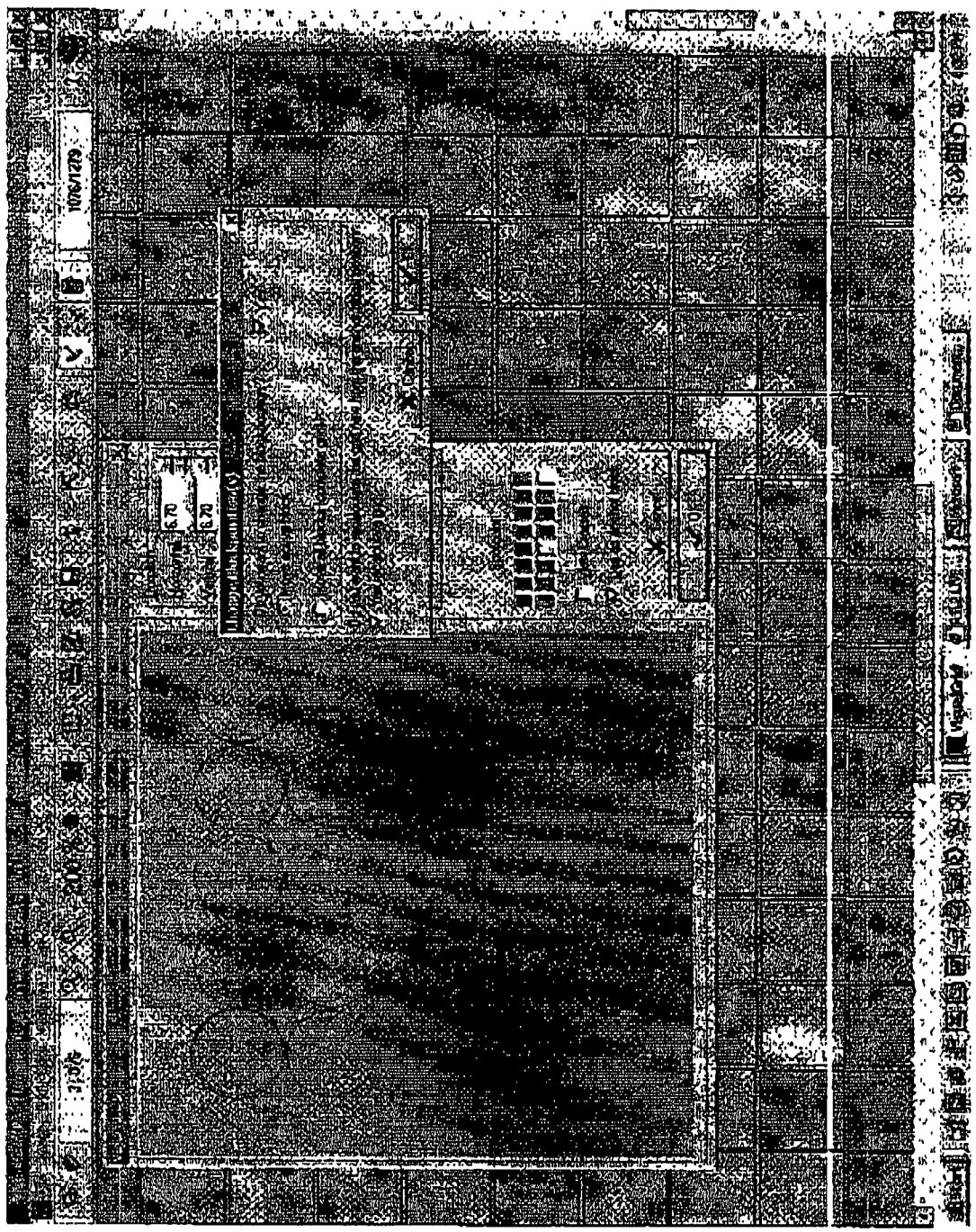

Excess blocking reagent was removed by washing in PBS-T for 5 min. Streptavidin-horseradish peroxidase was diluted 1:25,000 in 40 ml of PBS-T and added to the membrane in a Roller Blot hybridisation oven (Techne) for 1 h at room temperature. The membrane was then washed with 3 changes of PBS-T buffer for 5 min each. Detection of proteins was using chemiluminescent substrates for horseradish peroxidase (Amersham ECL reagent) and autoradiography. FIG. 5 shows the results of the Streptavidin screen for soluble protein. Results obtained from duplicate arrays uninduced and induced with IPTG prior to cell lysis (FIGS. 5a and 5b respectively) are shown. Evidence of IPTG-induced protein expression can be seen on the second membrane (5b).

An alternative, more quantitative method for detection uses fluorescence and is presented in addition to the chemiluminescent method above: The same library of the candidate gene was prepared as an array as above and then biotinylated proteins detected using a fluorescent Alexa488-streptavidin conjugate (Molecular Probes). The membrane was then scanned using a Typhoon imager (Amersham) and the image analysed using software VisualGrid (GPC Biotech) (FIG. 16).

Data Analysis

Signals from the array were quantified by densitometry and clones were ranked for expression level using image analysis software (5c) and prioritised for further study. Of the 27000 clones analysed, about 300 were selected for further analysis since the data indicated expression of soluble protein.

Analysis of Unselected and Selected Clones

Clones from the library of the previously unexpressed candidate gene of pHAR1111 which were identified as expressing soluble, stable protein from the array data were robotically extracted from the frozen bank using the re-arraying functionality of the picker-gridder robot. Insert size was screened using PCR screen of 96 clones with flanking primers and agarose gel electrophoresis. The same analysis was also performed on a random selection of clones from the library for comparison in order to determine the quality of the library. The PCR results to the randomly picked clones are displayed in FIG. 15. A graph showing the analysis of this PCR data is presented in FIG. 14 and it can be observed that there is a linear and relatively unbiased distribution of truncation lengths. The PCR products were digested using NdeI to confirm the start codon. The PCR analysis of clones identified as best soluble expressers from the fluorescence analysis is shown in FIG. 17 and it is clear that the distribution of truncation sizes is no longer random, but clusters around a similar size.

Protein expression of the first 96 best expressers (same library but from the earlier chemiluminescent detection method) was verified by western blot and it was confirmed that the proteins were soluble by filtration-based fractionation of expression lysates (FIG. 13) and matched the predicted insert size.

Solubly expressing clones of the previously unexpressed candidate gene were then sequenced using vector specific primers with sequence reading across the truncated gene to identify both the exact identity of the truncation boundaries and replicates (where the same clone was recovered multiple times). The latter occurs because, on average, each position of the protein was tested 7-fold. Using these data, experimentally determined clones were aligned against the full-length gene resulting in a soluble expression map (FIG. 11). Such a map is unique and has never been produced previously for a protein. It illustrates the positions in a protein where it can be truncated and produce soluble protein. Multiple clones are identified and these can be further prioritised by a) selecting those that give a high signal on the membrane array and western blots when probed with streptavidin i.e. express well b) selecting those that are smallest when consecutive amino acids are identified as truncation points. The latter is an advantage when clones are to be used for X-ray crystallography, as compact proteins with ordered termini usually crystallise more efficiently than proteins with appended, disordered peptide. This resolution of information is only possible due to the oversampling of the experiment made possible by the high throughput nature of the screening method.

As can be seen, there is a degree of order evident from portraying the degree of solubility of the various clones ranked according to the sequence of the encoding gene. Similar levels of solubility are evident in constructs with consecutive truncations (see straight lines drawn through marker points), and these are believed to correspond to regions of consecutive residues in solvent-exposed linkers. In contrast, gaps of poor solubility are evident from truncation boundaries that fall within structured regions in the protein (see region marked as "binding domain" in FIG. 11).

It is hypothesised herein that this type of analysis allows an exhaustive analysis of the solubility of truncated variants of a protein to divulge information on protein structure, such as domain boundaries, and the degree of solvent exposure of residues in the primary structure of the protein. This forms a further aspect of the present invention.

Protein Expression Colony vs Liquid

FIG. 13 shows Western blot analysis of positive clones grown up in LB culture medium, lysed and fractionated into soluble fractions. A wide range of expression level is evident, although 3 clusters of 10 k Da, 20 kDa and 30 kDa can be distinguished that are also apparent in the soluble expression map (FIG. 11). The full-length protein is 86 kDa and absence of larger constructs is thought to be a consequence of the architecture of this particular target. This result also demonstrates that protein expression as measured in colonies correlates well with that of the more standard liquid culture format.

Scale-Up of Protein Expression and Further Characterisation

One of the genetic constructs identified above as expressing purified protein was subcloned into a pTriEX derivative vector (Novagen) (FIG. 19) for improving protein expression through use of a stronger T7-based promoter and for aiding purification via addition of a N-terminal hexahistidine tag that can be removed by cleavage with TEV protease. Expression of this particular construct was good at approximately 40 mg per liter and lead to easily purifiable material. This is demonstrated by SDS-PAGE analysis of the purification fractions (FIG. 18). The purified protein shown here was further characterised for foldedness using NMR and the HSQC spectrum of $N^{15}$ labelled material is shown in FIG. 21. This particular protein has proceeded to a full structure solution by NMR showing that it does comprise a folded, soluble and globular domain from a protein that as never been overexpressed successfully before, thus demonstrating the utility of the current invention. The clone has also been used for crystallisation studies.

Additionally, a second larger 30 kDa protein of this target has been produced using the information from the soluble expression map to guide the selection of clones (FIG. 11) and comprises the smaller domain from above plus another 20 kDa of material. It is expected that this comprises at least two domains. This protein was effectively expressed from both the pTriEX system (FIG. 19) and also a pMAL vector (New England Biolabs) that produces an easily purifiable maltose binding protein fusion which is shown here in FIG. 20.

Analysis of NF-Kappa B: an Additional Example of the Invention Employing a Protein of Known Structure for Validation Purposes The first example shown above in detail was of a previously intractable protein since it was not possible to express the protein prior to this work. However it was also considered necessary to perform the same process on a protein of known structure in order to validate the method further. The protein NF-kappa B was chosen since it has a well-defined domain structure. Two libraries were constructed using pHAR1112 for N-terminal truncation (FIG. 2) and pMAS106 (FIG. 3) for C-terminal truncation. The libraries were constructed as for the example above with the exception that pMAS106 was digested with FseI and XbaI prior to the exonuclease truncation step.

Figure 6:
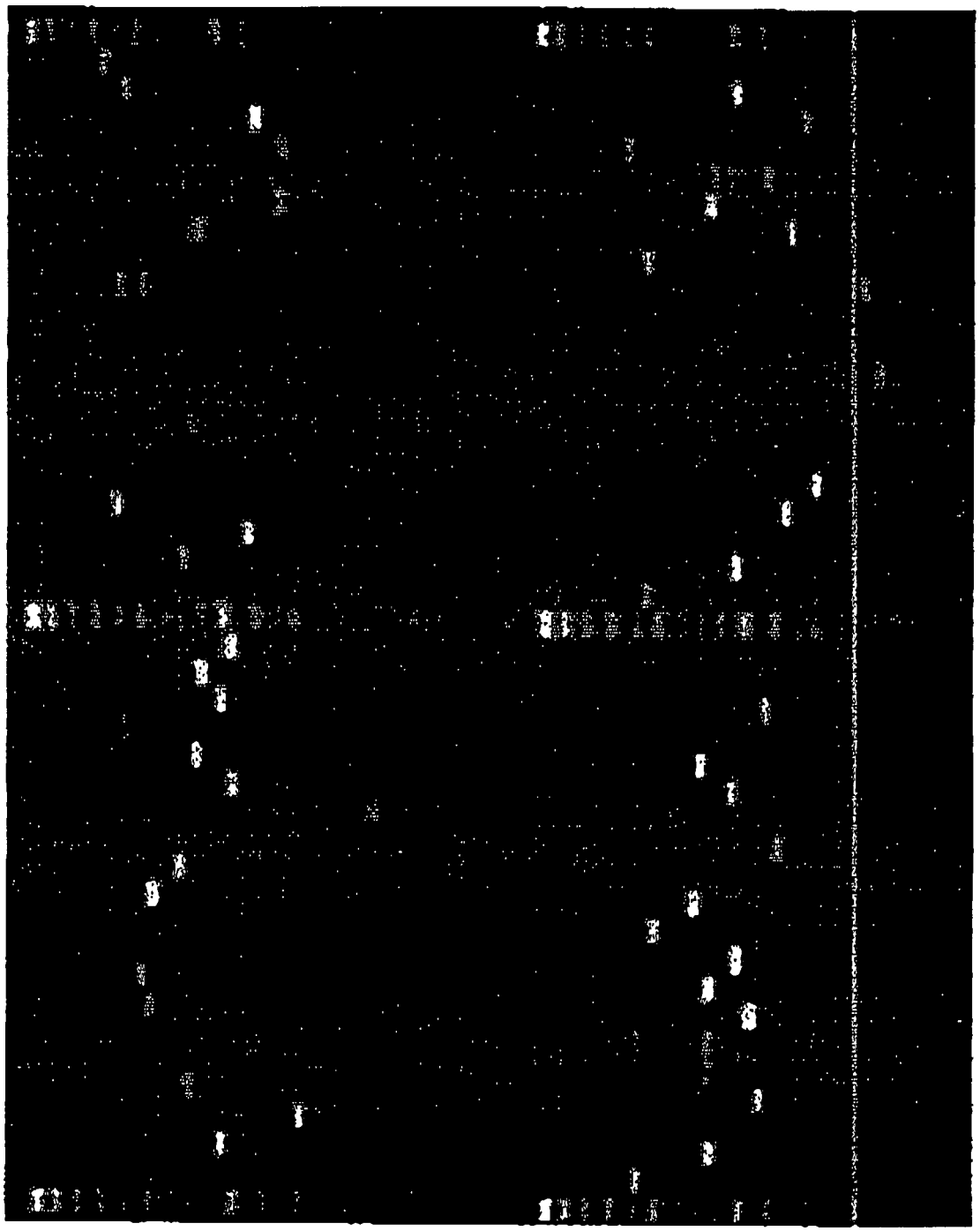
FIG. 6: Sizing of truncated NF-?B truncated inserts by PCR reveals a random size distribution.
Figure 7:
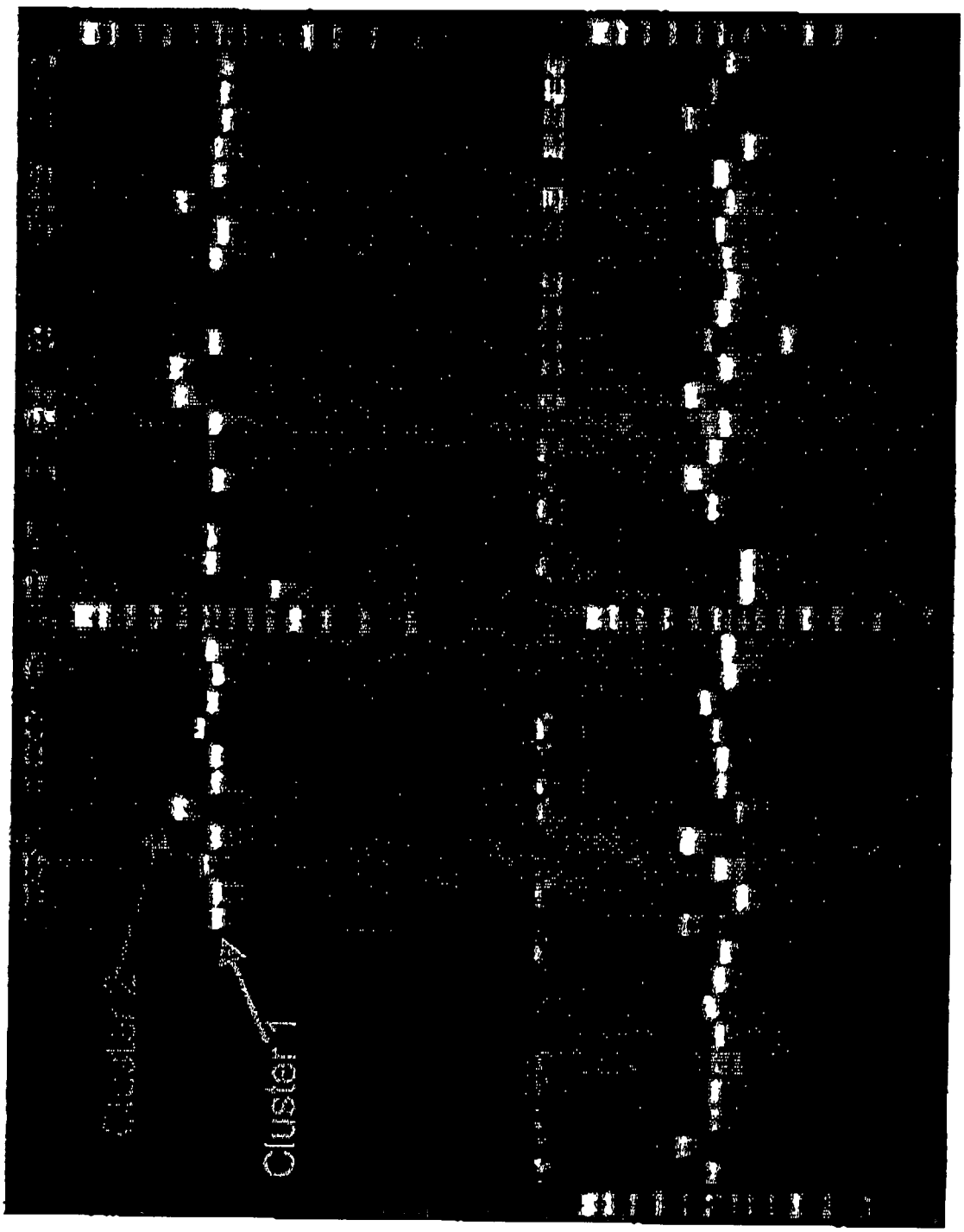
FIG. 7: DNA fragments sized by PCR of the expression plasmids using flanking is oligonucleotide primers. Clones expressing soluble truncated NF kappa B protein can be organised into 2 clusters indicative of one and two domain constructs (approximately 25 kDa and 40 kDa predicted size).
Figure 8:
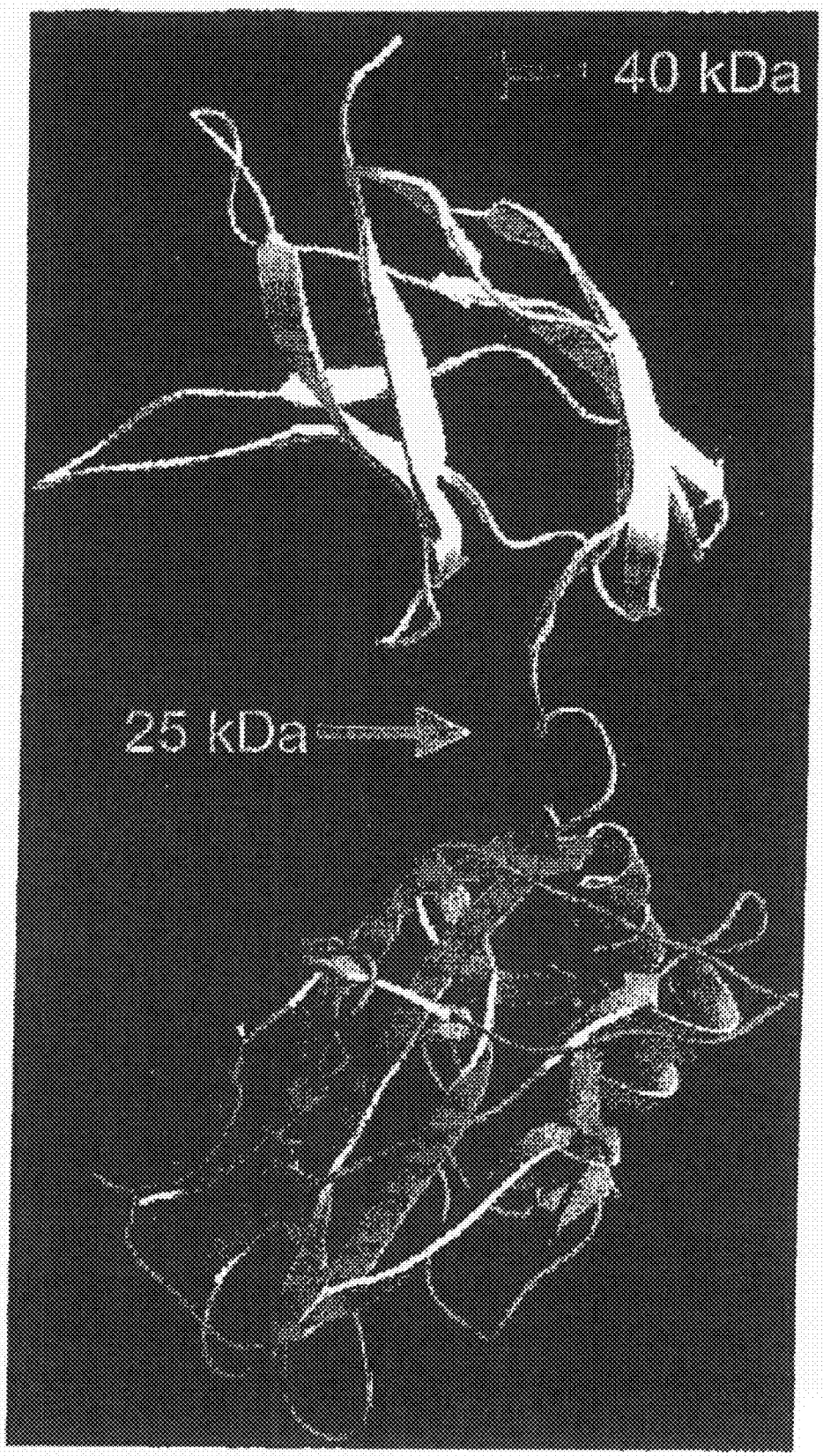
FIG. 8: Structure of the NF-?B protein indicating the size of the one and two domain protein fragments when truncated from the C-terminus.
Figure 9:
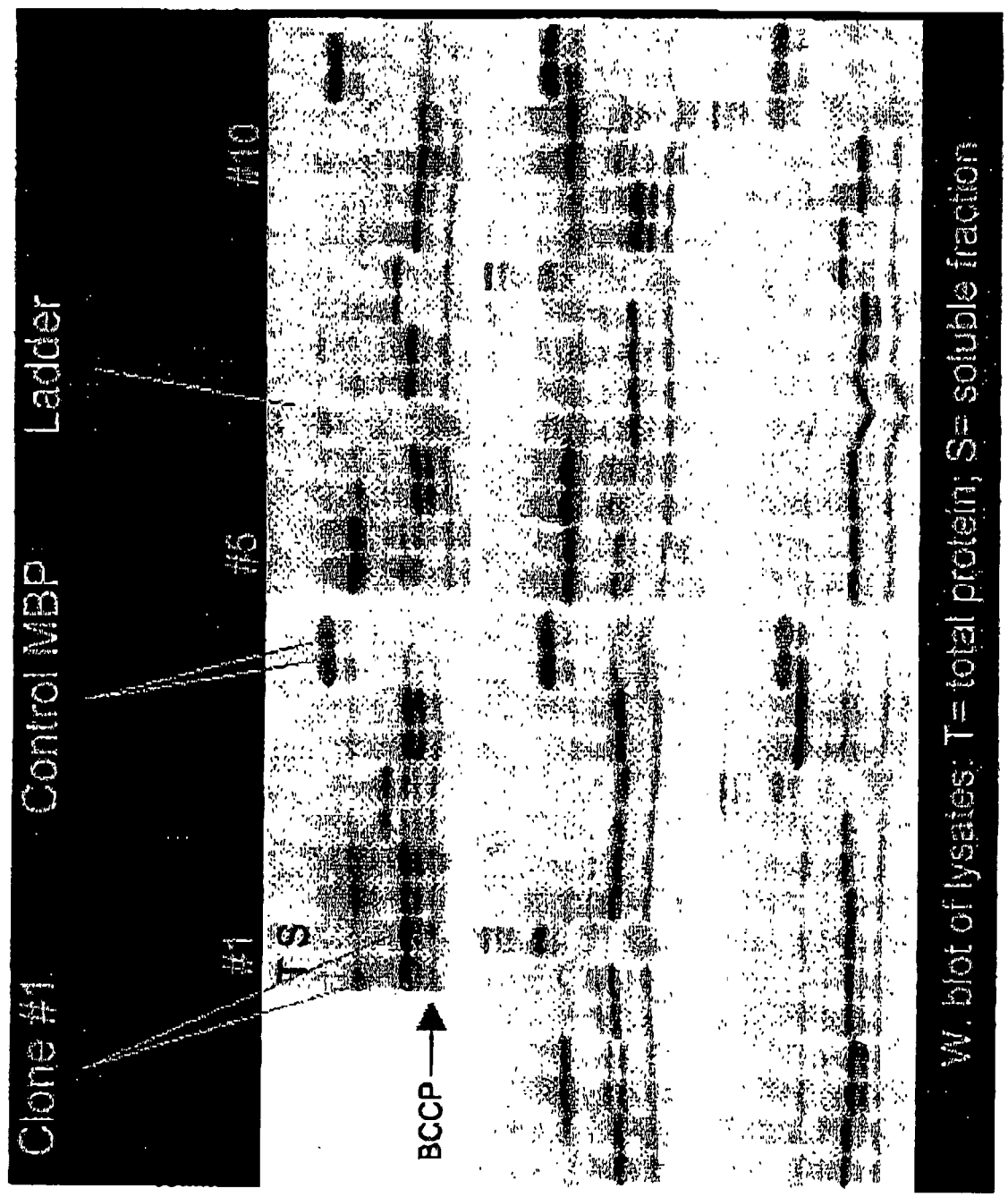
FIG. 9: Protein expression screen of the 48 best expressing NF-?B clones by Western blot. There is no significant difference between the total (T) and soluble (S) fractions for each clone indicating the clones identified by the screen are soluble. Faint expression of the E. coli endogenous BCCP protein is also visible since it is the only other biotinylated protein in the cell.

The quality of the C-terminal truncation library from pMAS106 was measured by PCR of the gene fragment inserts with flanking primers as above and the results are shown in FIG. 6. The array of colonies was analysed using the fluorescent method with Alexa488-streptavidin conjugate as described above. The positive clones were isolated from the main library using the cherrypicking function of the picker-gridder robot and the most intense 96 clones analysed by PCR. The results (FIG. 7) reveal 2 size clusters of DNA that are predicted to encode proteins of approximately 25 kDa and 40 kDa. These predicted sizes correlate well with the domain structure of NF-kappa B (FIG. 8). The first 48 clones were expressed in LB liquid cultures and total and soluble lysates were prepared. Analysis by western blot (FIG. 9) indicates that all proteins are totally soluble and that the protein sizes observed closely match the predicted sizes from the PCR screen (FIG. 7). All soluble clones were sequenced and the new C-termini generated by truncation were aligned against the protein sequence resulting in a soluble expression map for NF-kappa B (FIG. 10). The domain structure of the protein is clearly revealed and the edges of the domains mapped at single amino acid resolution by selecting the smallest, most compact form of each domain (FIG. 12). Both the two domain 40 kDa and one domain 25 kDa constructs have been previously characterised in the scientific literature as being functional for DNA binding. Thus the domains identified by the screening for soluble expression of the randomly truncated NF-kappa B gene are both soluble and functional.

Bi-Directional Truncation Protocol.

The vector used as the basis for the gene truncation library synthesis is a modified pET vector with kanamycin resistance and a T7 promoter system for high level *E. coli* expression of proteins (pTAR007—FIG. 25). This vector, used for bidirectional truncation, can also be used for unidirectional truncation depending on how the target gene is cloned. The salient points pertinent to the synthesis and screening of libraries for solubility are:

1. At the 5' end of the target gene, there is DNA encoding a hexahistidine tag and TEV cleavage site to aid protein purification and subsequent removal of the tag with TEV protease. In the desired end constructs, this tag is in frame with the target gene.
2. At the 3' end of the target gene, there is DNA encoding a biotin acceptor peptide that is used as an indicator of solubility of the gene product. In the desired end constructs, this tag is in frame with the target gene.
3. At each end of the target gene, there are two restriction sites. On the vector side, there are sites (NsiI or AatII) that leave a 3' overhang that is exonuclease III resistant. On the target end side, there are sites (NotI or AscI) that leave a 5' overhang that is an exonuclease III substrate.
4. If the gene is to be bidirectionally truncated, it is cloned as a AscI/NotI PCR fragment. In a first step, the vector is digested with AatII and AscI and treated with ExonucleaseIII and Mung Bean Nuclease as described above. The DNA is then size-separated by 0.5% (w/v) TBE agarose gel electrophoresis and the DNA ranging from full-length down to vector minus insert is excised from the gel, ligated and used to transform a high efficiency cloning strain of E. coli. Approximately 30,000 colonies are pooled and used to make a single plasmid preparation. This plasmid mix is then digested with NsiI and NotI and treated with ExonucleaseIII and Mung Bean Nuclease as described above. The DNA is again size-separated by 0.5% (w/v) TBE agarose gel electrophoresis and the DNA in the size range desired is again excised from the gel, ligated and used to transform a high efficiency cloning strain of E. coli. By desired size range, it is meant a collection of DNA fragments of a size range that may contain a particular domain within. For example, a kinase catalytic domain might on average be 300 amino acids long, encoded by 900 nucleotides. So DNA corresponding to [empty vector plus 600 nucleotides] to [empty vector plus 1200 nucleotides] is excised from the gel. When translated, those constructs in frame would encode protein fragments in the size range from 200 amino acids to 400 amino acids.
5. If the target gene is to be unidirectionally truncated at the 5' end to generate N-terminally deleted proteins, it is cloned as an AscI/NsiI PCR fragment. The vector is then digested with AatII and AscI and treated with ExonucleaseIII. The size range tested is from [empty vector] to [empty vector plus insert], i.e. the full range of truncated inserts. The DNA is then ligated to produce circular vector and used to transform a high efficiency cloning strain such as E. coli DH5alpha. Plasmid is prepared from a pooled mixture of, typically, 30,000 colonies and used to transform a protein expression strain such as E. coli BL21 RIL codon plus that is compatible with the T7 promoter system.
6. If the target gene is to be unidirectionally truncated at the 3' end to generate C-terminally deleted proteins, it is cloned as an AatII/NotI PCR fragment. The vector is then digested with NotI and NsiI and treated with ExonucleaseIII. The size range tested is from [empty vector] to [empty vector plus insert], i.e. the full range of truncated inserts. The DNA is then ligated to produce circular vector and used to transform a high efficiency cloning strain such as E. coli DH5alpha. Plasmid is prepared from a pooled mixture of, typically, 30,000 colonies and used to transform a protein expression strain such as E. coli BL21 RIL codon plus that is compatible with the T7 promoter system.

As described earlier, the screening is preformed by robotic picking and gridding followed by detection of protein expression via hybridisation of membranes. In an improvement that permits sensitive ranking of positive clones and therefore prioritisation of clones, the colony arrays are probed with fluorescent streptavidin e.g. labelled with Alexa488 dye. Detection may then be performed using a fluorescent imager such a Typhoon Imager (Amersham). The presence of a N-terminal hexahistidine tag permits parallel screening on the same membranes for the intact N-terminus of the protein using an antibody with a fluorescent dye (perhaps via a secondary, generic dye-labelled antibody). Thus colonies yielding a signal from the streptavidin hybridisation indicate that the protein is soluble and the presence of a histidine tag signal indicates that the protein is full-length. In this way, false positives resulting from internal initiation of translation within the gene, or premature termination of translation, may be simply screened out since presence of both ends of the protein indicates that it is full-length. Additionally, the presence of a hexahistidine tag permits rapid verification of solubility via a small-scale metal affinity chromatography column and secondly permits direct scale-up and purification of the truncated proteins.

Protein Expression from the pTAR007 Target Gene Library.

In a validation experiment, the pTAR007 system was used to truncate and express a target gene library of a viral protein. The methodology used was similar to that described above. FIG. 26 shows a graphical representation of the truncation method and indicates that the method allows for the whole of the target gene to be scanned.

The clones which showed the highest level of protein expression were selected and small scale expression trials carried out. FIG. 22 shows a representation of an SDS-PAGE gel of total protein compared to soluble protein for those clones showing the highest soluble protein expression. Colony 4, which showed the highest level of soluble protein expression was expressed in shaker flasks on a "liter scale" and the resulting protein was affinity purified (see FIGS. 23 & 24). Colony 4 yielded approximately 50 mg/L of culture and the resulting purified protein is now the subject of crystallisation trials.

The invention claimed is:

1. A method of generating a library of nucleic acid molecules of varying sizes, wherein each nucleic acid molecule forms an insert within a vector, and each vector comprises two pairs of restriction enzyme cleavage sites positioned so as to flank each side of the nucleic acid insert, the method comprising:
   a) cleaving a vector having a nucleic acid insert with a first pair of restriction enzymes which cleave at the pair of cleavage sites positioned in the vector on a flank of the nucleic acid insert such that an exonuclease-susceptible nucleic acid end results on an insert end of the vector and an exonuclease-resistant end results on a vector end;
   b) digesting the linearised vector using an exonuclease, followed by removal of single-stranded DNA;
   c) recircularising the vector by ligation of the exonuclease susceptible end and the exonuclease-resistant end;
   d) cleaving the recircularised vector with a second pair of restriction enzymes which cleave at the pair of cleavage sites positioned in the vector on a second flank of the nucleic acid insert, such that an exonuclease-susceptible nucleic acid end results on an insert end of the vector and an exonuclease-resistant end results on a vector end;
   e) digesting the linearised vector using an exonuclease, followed by removal of single-stranded DNA; and
   f) recircularising the vector by ligation;
wherein step a) is performed on a plurality of vectors having the same insert, to produce the library of nucleic acid molecules comprises nucleic acid inserts truncated at both ends wherein the orientation of each nucleic acid insert within each vector is the same.

2. The method according to claim 1, additionally comprising the step of amplifying the recircularised vectors.

3. The method according to claim 1, wherein in the cleavage steps, the exonuclease-susceptible nucleic acid end forms a 5'-overhang and the exonuclease-resistant end forms a 3'-overhang.

4. The method of claim 1, wherein the exonuclease is exonuclease III.

5. The method according to claim 1, wherein the pair of restriction enzymes consists of a first restriction enzyme selected from the group consisting of AatII, ApaI, BanII, BglI, BsfXI, HaeII, KpnI, NsiI, PstI, SacI and SphI; and a second restriction enzyme selected from the group consisting of AscI, BamHI, ClaI, Csp45I, EcoRI, EcoRV, HindIII, NcoI, NdeI, NotI, SalI, SmaI, SpeI, XbaI and XhoI.

6. The method according to claim 1, wherein samples of linearised vectors are digested using exonuclease for varied periods of time.

7. The method according to claim 1, wherein the number of samples is 2, 3, 4, 5, 10, 15, 20, 25, 30, 35, 40, 45, 50, 55, 60, 65, 70, 75, 80, 85, 90, 95, 100, 115, 130, 145, 160, 175, 190, 205, 220, or more.

8. The method according to claim 1, wherein the exonuclease digestion reactions in the samples are separated by 5, 10, 15, 20, 25, 30, 45, 60, 90, 120, 180, 300, 450 or more seconds.

9. The method according to claim 1, wherein the coding region for a peptide substrate flanks the sequence of the nucleic acid insert at one terminus, such that the peptide is genetically fused to the protein sequence coded for by the insert sequence upon expression.

10. The method according to claim 1, wherein the coding region for a purification tag flanks the sequence of the nucleic acid insert at one terminus, such that the peptide is genetically fused to a protein sequence coded for by the insert sequence upon expression.

11. The method according to claim 1, wherein the vector used is a plasmid vector.

12. The method according to claim 1, additionally comprising transforming a suitable host cell with the recircularised vectors.

13. The method according to claim 12, additionally comprising the step of growing the transformed cells and separating the vectors from the transformed cells.

14. The method according to claim 13, wherein the host cell is a bacterial cell.

15. The method according to claim 14, wherein the bacterial cell is selected from the strains DH5α or BL21.

* * * * *